US008273403B2

(12) United States Patent
Barden et al.

(10) Patent No.: US 8,273,403 B2
(45) Date of Patent: Sep. 25, 2012

(54) GENERATION OF SURFACE COATING DIVERSITY

(75) Inventors: Michael C. Barden, St. Lucia (AU); Peter A. Kambouris, Eight Mile Plains (AU)

(73) Assignee: Bio-Layer Pty Ltd., Queensland (AU)

( * ) Notice: Subject to any disclaimer, the term of this patent is extended or adjusted under 35 U.S.C. 154(b) by 1485 days.

(21) Appl. No.: 10/514,070

(22) PCT Filed: May 9, 2003

(86) PCT No.: PCT/AU03/00566

§ 371 (c)(1), (2), (4) Date: Mar. 10, 2005

(87) PCT Pub. No.: WO03/095494

PCT Pub. Date: Nov. 20, 2003

(65) Prior Publication Data

US 2006/0083858 A1 Apr. 20, 2006

Related U.S. Application Data

(60) Provisional application No. 60/379,966, filed on May 10, 2002.

(51) Int. Cl.
*B05D 5/00* (2006.01)
*G01N 33/48* (2006.01)

(52) U.S. Cl. .... 427/2.13; 427/212; 427/402; 427/407.1; 427/407.2; 427/409; 427/412.1; 427/429; 427/430.1; 427/496; 427/508; 427/551; 427/553

(58) Field of Classification Search ............... 427/407.1, 427/2.11, 2.12, 2.13, 402, 407.2, 409, 412.1, 427/212, 214, 222, 429, 430.1, 508, 509, 427/553, 557, 558, 496, 551; 435/287.1, 435/287.2, 288.3; 436/501, 518, 524, 525, 436/528, 531
See application file for complete search history.

(56) References Cited

U.S. PATENT DOCUMENTS 3,286,009 A 11/1966 Yumoto
3,849,172 A 11/1974 Chin et al.
4,205,952 A 6/1980 Cais
4,267,202 A 5/1981 Nakayama et al.
4,799,931 A 1/1989 Lindstrom
4,985,468 A 1/1991 Elmes et al.
5,047,445 A 9/1991 Nishizawa
5,080,924 A 1/1992 Kamel et al.
5,130,343 A 7/1992 Frechet et al.
5,139,817 A 8/1992 Abe et al.
5,238,613 A 8/1993 Anderson
5,244,799 A 9/1993 Anderson
5,364,907 A 11/1994 Rolando et al.
5,384,265 A 1/1995 Kidwell et al.
5,451,453 A 9/1995 Gagnon et al.
5,583,211 A 12/1996 Coassin et al.
5,683,800 A 11/1997 Stringfield et al.
5,691,431 A 11/1997 Chen et al.
5,789,487 A 8/1998 Matyjaszewski et al.
5,807,937 A 9/1998 Matyjaszewski et al.
5,832,102 A 11/1998 Uchida
5,886,104 A * 3/1999 Pedersen et al. .............. 525/242
5,922,161 A 7/1999 Wu et al.
5,922,545 A 7/1999 Mattheakis et al.
5,932,102 A 8/1999 Wyllie et al.
5,976,813 A 11/1999 Beutel et al.
6,001,894 A 12/1999 Ottersbach et al.
6,013,170 A 1/2000 Meade
6,060,530 A 5/2000 Chaouk et al.
6,110,369 A 8/2000 Ditter et al.
6,150,459 A 11/2000 Mayes et al.
6,225,368 B1 5/2001 D'Agostino et al.
6,226,603 B1 5/2001 Freire et al.
6,310,149 B1 10/2001 Haddleton
6,329,209 B1 12/2001 Wagner et al.
6,346,413 B1 2/2002 Fodor et al.
6,403,368 B1 6/2002 Jan et al.
6,515,039 B1 2/2003 Ulbricht et al.
6,582,754 B1 6/2003 Pasic et al.
6,706,320 B2 3/2004 Filippou et al.
6,858,309 B2 2/2005 Kambouris et al.
7,144,979 B2 12/2006 Maeji et al.
7,881,871 B2 2/2011 Gorse
2002/0025380 A1 2/2002 Vanmaele et al.
2003/0003223 A1 1/2003 Morse et al.
2003/0215877 A1 11/2003 Love et al.
2004/0091874 A1 5/2004 Yamasaki et al.
2004/0112832 A1 6/2004 Sundberg et al.
2006/0134717 A1 6/2006 Tellier et al.
2006/0139468 A1 6/2006 Wada

FOREIGN PATENT DOCUMENTS

CA 2052783 4/1992
(Continued)

OTHER PUBLICATIONS

U.S. Appl. No. 10/109,777, filed Mar. 28, 2002.

(Continued)

*Primary Examiner* — William Phillip Fletcher, III
(74) *Attorney, Agent, or Firm* — Morgan, Lewis & Bockius LLP

(57) ABSTRACT

This invention relates to a surface discovery system and high-throughput combinatorial synthesis methods for generating large numbers of diverse surface coatings on solid substrates. The system is built upon a synthon which comprises at least three elements: a chemical backbone coating on the solid substrate that comprises a copolymer (B) of at least one passive constituent (P) and at least one active constituent (A); a spacer unit (S) separating the backbone from a functional group; and a functional group (F). The methods comprise the following steps: 1) selecting a plurality of synthons so that each synthon has at least two points of diversity selected from P, A, S and F; 2) applying copolymer B onto a substrate; and 3) attaching a combination of S and F to constituent A of copolymer B. Steps 2) and 3) are performed such that different synthons are generated on localized regions of the substrate.

33 Claims, 12 Drawing Sheets

FOREIGN PATENT DOCUMENTS

| | | |
|---|---|---|
| CA | 2341387 | 3/2000 |
| CA | 2249955 | 4/2000 |
| EP | 0060138 | 3/1982 |
| EP | 0231918 | 2/1987 |
| EP | 0342068 | 4/1989 |
| EP | 0311989 | 1/1993 |
| EP | 0837080 | 4/1998 |
| EP | 0947544 | 10/1999 |
| EP | 0972566 | 1/2000 |
| EP | 1072635 | 7/2000 |
| GB | 0856329 | 12/1960 |
| GB | 0935013 | 8/1963 |
| GB | 1138287 | 12/1968 |
| GB | 02199786 | 7/1988 |
| JP | 1275639 | 11/1989 |
| JP | 3065341 | 3/1991 |
| JP | 8259716 | 8/1996 |
| JP | 2000-514799 | 11/2000 |
| JP | 2001-261758 | 9/2001 |
| JP | 2002-155228 | 5/2002 |
| JP | 2001-157574 | 12/2002 |
| JP | 2003-344404 | 12/2003 |
| JP | 2004-004097 | 1/2004 |
| JP | 2004-020328 | 1/2004 |
| JP | 2006-157600 | 6/2006 |
| JP | 2010-505910 A | 2/2010 |
| WO | WO 90-02749 | 3/1990 |
| WO | WO 90-07575 | 7/1990 |
| WO | WO 91-07687 | 5/1991 |
| WO | WO 92-05696 | 4/1992 |
| WO | WO 95/09176 | 4/1995 |
| WO | WO 97-02310 | 1/1997 |
| WO | WO 97-47661 | 12/1997 |
| WO | 98/00435 | 1/1998 |
| WO | WO 98-01480 | 1/1998 |
| WO | WO 98-31732 | 7/1998 |
| WO | WO 99-28352 | 6/1999 |
| WO | WO 00/12575 | 3/2000 |
| WO | WO 00-78740 | 12/2000 |
| WO | WO 01-62804 | 8/2001 |
| WO | WO 02/50171 | 6/2002 |
| WO | WO 03-000708 | 1/2003 |
| WO | WO 03-042249 | 5/2003 |
| WO | WO 03-095494 | 11/2003 |
| WO | 2004-011401 A2 | 2/2004 |
| WO | WO 2004-055518 | 7/2004 |
| WO | 2008-043788 A2 | 4/2008 |

OTHER PUBLICATIONS

Rich, et al., "Advances in Surface Plasmon Resonance Biosensor Analysis", *Current Opinion in Biotechnology*, 11:54-61 (2000).
Ruiz-Taylor, et al., "Monolayers of derivaitzed poly(L-lysine)-grafted poly(ethylene glycol) on metal oxides as a class of biomolecular interfaces", *PNAS*, 98(3):852-857 (2001).
Stolowitz, et al., "Phenylboronic Acid-Salicylhdroxamic Acid Bioconjugates. 1. A Novel Boronic Acid Complex for Protein Immobilization", *Bioconjugate Chemistry*, 12:229-239 (2001).
Supplementary European Search Report (Jul. 4, 2005).
International Search Report (Jul. 1, 2003).
U.S. Appl. No. 10/052,907 Restriction requirement dated Aug. 13, 2003.
U.S. Appl. No. 10/052,907 Non-final office action dated May 13, 2004.
U.S. Appl. No. 10/052,907 Final office action dated Dec. 21, 2004.
U.S. Appl. No. 10/052,907 Advisory Action dated May 12, 2005.
U.S. Appl. No. 10/052,907 Non-final office action dated Jul. 27, 2005.
U.S. Appl. No. 10/451,720 Non-final office action dated May 28, 2004.
U.S. Appl. No. 10/451,720 Non-final office action dated Dec. 28, 2004.
U.S. Appl. No. 10/451,720 Non-final office action dated Aug. 12, 2005.
U.S. Appl. No. 10/451,720 Notice of Allowance dated Aug. 11, 2006.
U.S. Appl. No. 10/109,777 Non-final office action dated May 21, 2003.
U.S. Appl. No. 10/109,777 Notice of Allowance dated Dec. 5, 2003.
U.S. Appl. No. 10/582,423 Restriction Requirement dated Mar. 20, 2009.
U.S. Appl. No. 10/582,423 Non-final office action dated Jun. 2, 2009.
U.S. Appl. No. 10/451,807 Restriction Requirement dated Dec. 19, 2005.
Angot, S., et al., "Living Radical Polymerization Immobilized on Wang Resins: Synthesis and Harvest of Narrow Polydipersity Poly(methacrylate)s," Macromolecules, vol. 34, pp. 768-774 (2001).
Berg, R., et al., "Long-Chain Polystyrene-Grafted Polyethylene Film Matrix: ?A New support for Solid-Phase Peptide Synthesis," J. Am Chem. Soc., vol. 111, pp. 8024-8026 (1989).
Boer, B., et al., "Microporous Honeycomb-Structured Films of Semiconducting Block Copolymers and Their Use as Patterned Templates," Advanced Materials, vol. 12, No. 21, pp. 1581-1583 (2000).
Daeyaert, F., et al., "A Pharmacophore Docking Algorithm and Its Application to the Cross Docking of 18- HIV-NNRTI's in their Binding Pockets," Proteins: Structure, Function, and Bioinformatics, vol. 54, pp. 526-533 (2004).
Darling, T., et al., "Living Polymerization: Rationale for Uniform Terminology," J. Polym. Sci. Part A: Polym. Chem., vol. 38, pp. 1706-1708 (2000).
Derwent Abstract Accession No. 1991-127943 and JP-03-065341 (XP002394884).
Derwent Abstract Accession No. 2001-499482 and JP-2001-158847.
Derwent Abstract Accession No. 89-367670, and JP 1-275639 A.
Derwent Abstract Accession No. 96-502794, and JP 8-259716 A.
Ejaz, M., et al., "Controlled Grafting of a Wall-Defined Glyco-polymer on a Solid Surface by Surface-Initiated Atom Transfer Radical Polymerization," Macromolecules, vol. 33, pp. 2870-2874 (2000).
European Supplemental Partial Search Report of EP 01271412 dated May 13, 2004.
European Supplementary Search Report of EP 01271084 dated May 19, 2004.
European Supplementary Search Report of EP 02712637 dated Aug. 16, 2006.
European Supplementary Search Report of EP 05756657 dated Feb. 26, 2009.
Granel, C., et al., "Controlled Radical Polymerization of Methacrylic Monomers in the Presence of a Bis(ortho-chelated) Arylnickel(II) Complex and Different Activated Alkyl Halides," Macromolecules, vol. 29, pp. 8576-8582 (1996).
Hawker, C., et al., "Radical Crossover in Nitroxide Mediated 'Living' Free Radical Polymerizations," J. Am. Chem. Soc., vol. 118, pp. 11467-11471 (1996).
Hori, M., et al., "Investigating Highly Crosslinked Macroporous Resins for Solid-Phase Synthesis," Biorganic & Med. Chem. Letters, vol. 8, pp. 2363-2368 (1998).
International Preliminary Report on Patentability of PCT/AU2005/000966 dated Jan. 9, 2007.
International Search Report of PCT/AU01/01638 dated Jan. 22, 2002.
International Search Report of PCT/AU2004/001747 dated Feb. 15, 2005.
International Search Report of PCT/AU2005/0009966 dated Aug. 3, 2005.
Jenekhe, S., et al., "Self-Assembly of Ordered Microporous Materials from Rod-Coil Block Copolymers," Science, pp. 372-375 (1999).
Karthaus, O., et al., "Water-Assisted Formation of Micrometer-Size Honeycomb Patterns of Polymers," Langmuir, vol. 16, No. 15, pp. 6071-6076 (2000).
Kato, M. et al., "Polymerization of Methyl Methacrylate with the Carbon Tetracloride/Dichlorotris-(triphenylphosphine)ruthenium(II)Methylaluminum Bis(2,6-di-tert-bu-tylphenoxide)Initiating System: Possibility of Living Radial Polymerization," Macromolecules, vol. 28, pp. 1721-1723 (1995).
Kunitake, T., "Self-Assembly of Polymers," Current Opinion in Colloid and Interface Sciences, vol. 6, pp. 1-2 (2001) Editorial Overview.
Lyne, P., "Structure-Based Virtual Screening: An Overview," Drug Discovery Today, vol. 7, pp. 1047-1055 (2002).

Machi, S., et al., "Effect of Swelling on Radiation-Induced Grafting of Styrene to Polyethylene," J. Polymer Science, vol. 8, pp. 3329, 3337 (1970).
Maiji, N. Joe, et al., "Grafted Supports Used with the Multipin Method of Peptide Synthesis," Reactive Polymers, vol. 22, pp. 203-212 (1994).
Mandal, T. et al., "Production of Hollow Polymeric Microspheres by Surface-Confined Living Radical Polymerization on Silica Templates," Chem. Mater., vol. 12, pp. 3481-3487 (200).
Maruyama, N., et al., "Mesoscopic Patterns of Molecular Aggregates on Solid Substrates," Thin Solid Films, 327329, pp. 854-856 (1998).
Muir, B.W., et al., "High-Throughput Optimization of Surfaces for Antibody Immobilization Using Metal Complexes," Analytical Biochemistry, vol. 363, No. 1, pp. 987-107 (2007) XP005910998.
Muller, K., et al., "Model and Stimulation of Multivalent Binding to Fixed Ligands," Analytical Biochemistry, vol. 261, pp. 149-158 (1998).
Needels, M., et al., "Generation and Screening of an Oligonucleotide-Encoded Synthetic Peptide Library," Proc. Natl. Acad. Sci. USA, vol. 90, pp. 10700-10704 (1993).
Nishikawa, T., et al., "Honeycomb-Patterned Thin Films of Amphiphilic Polymers as Cell Culture Substrates," Materials Science and Engineering, C vol. 8-9, pp. 495-400 (1999).
Nishikawa, T., et al., "Mesoscopic Patterning of Cell Adhesive Substrates as Novel Biofunctional Interfaces," Materials Science and Engineering, C vol. 10, No. 1-2, pp. 141-146 (1999).
Ookura, R., et al., "Stabilization of Micropatterned Polymer Films as Artificial Extracellular Matrices for Tissue Engineering, Molecular Crystals and Liquid Crystals Science and Technology Section A—Molecular Crystals and Liquid Crystals," vol. 337, pp. 461-464 (1999).
Patel, D., et al., "Applications of Small-Molecule Combinatorial Chemistry to Drug Discovery," DDT , vol. 1, No. 4, pp. 134-144 (1996).
Patten, T. et al., "Polymers with Very Low Polydispersities from Atom Transfer Radical Polymerization," Science, vol. 272, pp. 866-868 (1996).
Percec V., et al., "Living Radical Polymerization of Styrene Initiated by Arenesuljonyl Chlorides and $Cu^1(bpy)_nC1$," Macromolecules, vol. 28, pp. 7970-7972 (1995).
Rohr, J., "Combinatorial Biosynthesis—An Approach in the Near Future?" Agnew. Int. Ed. Engl., vol. 34, pp. 881-884 (1995).
Sackmann, E., et al., "Supported Membranes on Soft Polymer Cushions: Fabrication, Characterization and Applications," Tibtech February, vol. 18, pp. 58-64 (2000).
Schaaper, W., et al., "Synthesis of Large Nos. of Peptides for Rapid Screening of Bioactive Sequences," in J.A. Smith and J.E. River (Eds.), 12th American Peptide Symposium, Boston, MA, Jun. 16-21 (1991) Escom. Leiden, p. 651 (1992).
Shimomura, M., et al., "Bottom-up Strategy of Materials Fabrication: A New Trend in Nanotechnology of Soft Materials," Current Opinion in Colloid & Interface Sciences, (2001).
Stalmach, U., et al., Semiconducting Diblock Copolymers Synthesized by Means of Controlled Radical Polymerization Techniques, Journal of the American Chemical Society, vol. 122, pp. 5464-5472 (2000).
Tregear, G., "Graft Copolymers as Insoluble Supports in Peptide Synthesis," Chemistry and Biology of Peptides: Meienhofer, J., Ed., Ann Arbor Sci. Publ: Ann Arbor, MI, p. 175-178 (1972).
Turkova, "Oriented Immobilization of Biologically Active Proteins as a Tool for Revealing Protein Interactions and Function," Journal of Chromatogrpahy B., vol. 722, pp. 11-37 (1999).
Wang , J., et al., "Controlled/'Living' Radical Polymerization. Atom Transfer Radical Polymerization in the Presence of Transition-Metal Complexes," J. Am. Chem. Soc., vol. 117, pp. 5614-5615 (1995).
Widawski, G., et al., Self-organized honeycomb morphology of star-polymer polystrene films, Nature, vol. 369, pp. 387-389 (1994).
Written Opinion of PCT/AU2005/000966 dated Aug. 18, 2005.
Zhao, C., et al., "Polystyrene Grafted Fluoropolymer Micro Tubes: New Supports for Solid-Phase Organic Synthesis with Useful Performance at High Temperature," J. Combinatorial Chemistry, vol. 1, pp. 91-95 (1999).
Zheng, Y., et al., Biosensor Immunosurface Engineering Inspired by B-Cell Membrane-Bound Antibodies: Modeling and Analysis of Multivalenet Antigen Capture by Immobilized Antibodies, IEEE Transactions on Nanobioscience, vol. 2, No. 1, pp. 14-25 (2003).
U.S. Appl. No. 10/582,423 Non-final office action dated Jan. 13, 2010.
U.S. Appl. No. 10/582,423 Examiner Interview Summary dated Sep. 17, 2010.
U.S. Appl. No. 11/571,422 Restriction Requirement dated Feb. 3, 2010.
U.S. Appl. No. 11/571,422 Restriction Requirement dated May 19, 2010.
U.S. Appl. No. 11/571,422 Non-final office action dated Sep. 1, 2010.
Gold, E.R., et al., "Chromic Chloride: A Coupling Reagent for Passive Hemagglutination Reactions," The Journal of Immunology, vol. 99, No. 5, pp. 859-866 (1967).
Penzol, et al., Use of Dextrans as Long and Hydrophilic Spacer Arms to Improve the Performance of Immobilized Proteins Acting on Macromolecules Biotechnology and Bioengineering, vol. 60, pp. 518-523 (1998).
U.S. Appl. No. 11/571,422 Final office action dated Mar. 1, 2011.
U.S. Appl. No. 12/158,963 Restriction Requirement dated Jan. 28, 2011.
Johnson, D., et al., "Controlling Protein Orientation at Interfaces Using Histidine Tags: An Alternative to Ni/NTA," J. Am. Chem. Soc., vol. 127, pp. 2018-2019 (2005).
U.S. Appl. No. 10/502,907, filed Jan. 17, 2002, abandoned.
U.S. Appl. No. 10/466,743, filed Jan. 17, 2002, abandoned, which is a national stage application of PCT/AU02/00043.
U.S. Appl. No. 10/451,807, filed Dec. 19, 2001, abandoned, which is a national stage application of PCT/AU01/01639.
U.S. Appl. No. 12/158,963, filed Dec. 29, 2006, abandoned, which is a national stage application PCT/AU06/02010.
U.S. Appl. No. 11/571,422, filed Jun. 30, 2006, which is a national stage application of PCT/AU2005/000966.

* cited by examiner

GENERATION OF SURFACE COATING DIVERSITY

This application is a National Stage of International Application PCT/AU03/00566, filed May 9, 2003, which published as WO 03/095494 A1 on Nov. 20, 2003 under PCT Article 21(2) in English, and which, claims the priority of U.S. Provisional Patent Application No. 60/379,966, filed May 10, 2002.

FIELD OF THE INVENTION

The present invention relates to surface coating technology. In particular, the invention relates to a method for generating a library of different surface coatings on a substrate, to a method for optimising a substrate surface for a solid phase application and arrays or beads possessing discrete regions of particular optimised surface coatings.

BACKGROUND OF THE INVENTION

Current surface coating technology provides a relatively limited number of established surfaces that may be used in new solid-phase chemical or biochemical applications. The lack of established surfaces stems primarily from the difficulty associated with the generation of different surface coatings. While large numbers of chemically diverse compounds may now be generated in solution without too much difficulty, the ability to graft these molecules on to a solid phase and create a large number of surface coatings has proven a much more difficult problem to solve. In particular, the chemistry of grafting molecules onto solid phases to create surface coatings is highly unpredictable, and has to date remained more an art than a science.

There are numerous applications where a diverse range of novel surface coatings would be particularly advantageous, for example in the area of solid phase biological assays. With the number of novel proteins growing each day, there is growing need for novel solid phase surfaces that are compatible with the immobilization of these complex macromolecules. Despite this need, in practice there are to date relatively few solid surfaces available across the wide range of solid phase applications used to study biological molecules. For example, in the area of capture and display of biomolecules each commercial supplier has its own particular solid phase surface embodiment that is prescribed across a broad range of specific applications. One specific example is a surface generated using the well-established PEG chemistry as described in an article by Ruiz-Taylor et al. ("Monolayers of derivatized poly(L-lysine)-grafted poly(ethylene glycol) on metal oxides as a class of biomolecular interfaces," PNAS USA 98: 852-857 (2001)). Another example is the relatively new boronic acid complex chemistry used to prepare surfaces for immobilization of proteins described by Stolowitz et al. ("Phenylboronic Acid-Salicylhydroxamic Acid Bioconjugates. 1. A Novel Boronic Acid Complex for Protein Immobilization," Bioconjugate Chemistry 12: 229-239 (2001)).

Surface plasmon resonance (SPR) has now been widely adopted as a technique for detecting protein-ligand and protein-protein binding interactions. However the utility of SPR with a particular protein system depends greatly on the vagaries of how that macromolecule binds to the surface of the solid substrate when immobilized. If a particular SPR surface causes a protein of interest to bind in an orientation that is unfavorable for detecting ligand binding, there are only a handful of alternative surfaces with a limited range of binding properties from which to choose (see, e.g. Rich and Myszka "Advances in surface plasmon resonance biosensor analysis," Current Opinion in Biotechnology 11: 54-61 (2000)).

Similarly, mass spectrometry also is now widely employed for the analysis of biological macromolecules. These methods typically involve immobilization of a protein on a surface of substrate where it is then exposed to a ligand binding interaction. Following ligand binding (or non-binding) the molecule is desorbed from the surface and into a spectrometer using a laser (see, e.g. Merchant and Weinberger, "Recent advancements in surface-enhanced laser desorption/ionization-time of flight-mass spectrometry," Electrophoresis 21: 1164-1177 (2000)). As in the SPR experiment, the success of the mass spectrometry experiment depends largely on the interaction between the immobilized protein and the surface. In view of the thousands of proteins with different surface interactions, there is clearly a need for a large number of different substrate surfaces in order for mass spectrometry to be applied successfully to the high throughput analysis of the proteome.

Accordingly, the inability to provide a diverse array of surface coatings stands as an impediment to development in solid phase biological technologies such as biological assays and diagnostics, and biomaterials. Such an impediment also extends across a broad spectrum of other technologies, ranging from solid-phase chemical synthesis, catalysis development and separation and purification technologies.

SUMMARY OF THE INVENTION

In one aspect, the present invention provides a method of generating a library of different surface coatings on a substrate comprising:

a) selecting a surface coating synthon of formula B-S-F, wherein B is a copolymer of at least one passive constituent P and at least one active constituent A, S is a spacer unit and F is a chemical or biological functional group, wherein S is attached to an active constituent A of copolymer B, and wherein the synthon has at least one point of diversity selected from P, A, S and F;

b) applying backbone coating(s) of the selected copolymer B onto a substrate;

c) attaching the selected combination(s) of spacer unit S and functional group F to an active constituent A of copolymer B according to said selected synthon;

wherein steps b) and c) are performed such that surface coatings according to the synthon are generated on localised regions of the substrate, thereby providing said library of different surface coatings on the substrate.

In another aspect, the present invention provides a method of optimizing a substrate surface for a solid-phase application involving immobilization of a molecule comprising:

a) generating a library of different surface coatings on a substrate by a method comprising:

1) selecting a surface coating synthon of formula B-S-F, wherein B is a copolymer of at least one passive constituent P and at least one active constituent A, S is a spacer unit and F is a chemical or biological functional group, wherein S is attached to an active constituent A of copolymer B, and wherein the synthon has at least one point of diversity selected from P, A, S and F;

2) applying backbone coating(s) of the selected copolymer B onto a substrate;

3) attaching the selected combination(s) of spacer unit S and functional group F to an active constituent A of copolymer B according to said selected synthon;

wherein steps 2) and 3) are performed such that surface coatings according to the synthon are generated on localised regions of the substrate, thereby providing said library of different surface coatings on the substrate;

b) exposing at least two of the surface coatings in the library to the molecule to be immobilized; and c) determining which of the at least two surfaces results in better performance of the immobilized molecule in the solid-phase application.

In a further aspect, the present invention provides a biological molecule detection unit capable of detecting at least two biological molecules, said unit comprising a substrate having a plurality of surface coatings wherein at least two of said coatings are different, and tailored to recognise, bind to or associate with a particular biological molecule. A person skilled in the art would be able to adapt the methods described herein to prepare such a detection unit.

The present invention provides a method for generating a library of different surface coatings on a substrate which can be advantageously used as part of a surface discovery system. The library is generated using a unique synthon approach that provides an architectural framework from which the specific surface coatings can be realised.

The present invention fills a critical gap in solid surface technology by providing a high-throughput platform for the rational generation and exploration of surface coatings with novel molecular and macroscopic properties. The diverse combinatorial libraries of surface coatings that may be generated in a high-throughput manner using the synthon-based approach disclosed herein may be applied across a broad spectrum of technologies, ranging from solid-phase chemical synthesis, catalysis development, separation and purification technologies, biological assays and diagnostics, and biomaterials development.

DESCRIPTION OF THE PREFERRED EMBODIMENTS

The Synthon

As used herein the term "synthon" is used to refer to a fundamental chemical unit, or building block, which provides an architectural framework to design and develop a diverse array of surface coatings on a substrate. The synthon comprises three basic elements and can simplistically be represented as B-S-F, wherein B is a copolymer of at least one passive constituent P and at least one active constituent A, S is a spacer unit and F is a chemical or biological functional group. The spacer unit S is attached to an active constituent A of copolymer B, and the synthon has at least one point of diversity selected from P, A, S and F.

Together, the space unit and the functional group form a "functional tether" that may be modified further with chemical entities. Simple combinatorial chemical variation of the four points of diversity (i.e. passive constituent, active constituent, spacer unit, and functional group) of the synthon described above allows one to generate potentially thousands of unique but related surfaces. Systematic variation of the active constituent, passive constituent, spacer unit and functional group allows generation of libraries of different surface coatings that span a spectrum of microscopic and macroscopic properties. These libraries of surfaces may be further explored using a variety of analysis techniques to discover the optimal surface for a variety of applications. Consequently, the synthon-based approach to generating surface coating diversity described herein provides a platform akin to combinatorial synthesis of small molecules and peptide libraries.

Although combinatorial approaches to generating molecular diversity have been employed to generate new lead compounds in the drug discovery process, these strategies have not to date been employed in the search for novel surface coatings that exhibit advantageous properties. Indeed, the standard solid phase combinatorial chemistry approaches used in drug discovery focus on generating variety in the small molecule properties and avoid diversity in the solid phase to which it is attached. The solid phase is viewed simply as a convenient handle to be disposed of after cleavage of the small molecule. Consequently, there has been little systematic exploration of solid phase surfaces and how their properties may be varied to optimize solid phase applications.

Figure 1:
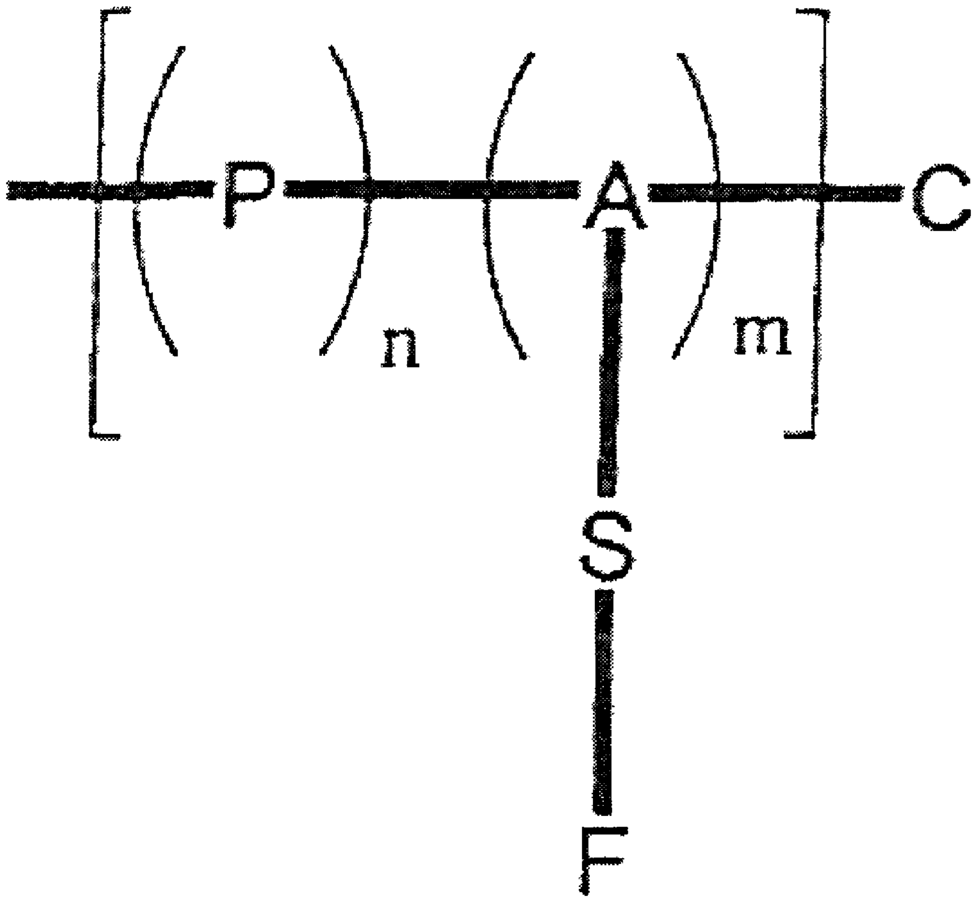
FIG. 1 illustrates a more detailed representation of a potential structure of the synthon.

Together, the space unit and the functional group form a "functional tether" that may be modified further with chemical entities. In FIG. 1, the synthon further comprises a control agent C which may be optionally attached to copolymer B, as represented by -[P-A]-. The control agent C may be used as a means to prepare copolymer B under living/controlled polymerization conditions, or alternatively as a means to modify copolymer B. Preferred control agents include, but are not limited to, RAFT control agents, ATRP control agents, and nitroxide control agents. The use of a control agent advantageously provides a means to carefully control and design the molecular architecture of copolymer B, for example by controlling molecular weight distribution and/or distribution of monomeric units within the copolymer chain.

Simple combinatorial variation of the four points of diversity (i.e. passive constituent, active constituent, spacer unit, and functional group) that form the basic synthon described above allows one to generate potentially thousands of unique but related surfaces. In one preferred embodiment, the diversity is derived solely from the spacer unit S. In another preferred embodiment, the diversity is derived solely from the functional group F. In yet another preferred embodiment, the diversity is derived from both the spacer unit S and the functional group F.

In a relatively simple example, starting with one backbone coating on a base material (i.e. where the P and A constituents are kept constant) treatment with at least ten spacer unit S variants, and 10 different transformations of the functional group F, results in 100 different surfaces.

Of course, greater numbers of diverse compounds may be achieved if a control agent C is incorporated as another point of diversity. The control agent may be used as the start site for living-controlled polymerization reactions. Consequently, the backbone coating may be modified by living-controlled polymerization independent of modifications at the spacer attached to the active constituent of the backbone.

Additionally, diversity may be achieved by utilizing orthogonal reaction strategies and/or combining mixtures of elements in building the synthons. For example, the passive constituent may act as a second active constituent by modifying it using a reaction orthogonal to that used to modify the first active constituent. Consequently, in some embodiments both the active and passive constituents may be modified with spacers to generate greater surface diversity.

Advantageously, the present invention allows construction of libraries comprising preferably at least 10, more preferably at least 100, still more preferably at least 1000, most preferably at least 10,000 different surface coatings.

Preferably, the library in accordance with the present invention is prepared in a multiplex format, and the library is also used in a multiplex format.

The Backbone Coating and its Parameters

The present invention involves applying backbone coating(s) of the selected copolymer B onto a substrate. The backbone coating provides the macroscopic design element in the method and is preferably covalently bound to the underlying substrate. In a preferred embodiment, the backbone coating is bound to the underlying substrate through well-known methods of polymer grafting, or other methods of coating a solid substrate such as dip coating, plasma polymerization, vapor deposition, stamp printing, gamma irradiation, electron beam exposure, thermal and photochemical radiation.

As the backbone coating, copolymer B comprises at least one passive constituent P and at least one active constituent A. These constituents may be viewed as monomeric units within the copolymer B. The copolymer B may also comprise other monomeric units. In some embodiments, the backbone coating may comprise more than one active and more than one passive constituent. As described in greater detail below, the active and passive constituents may be selected from a wide spectrum of compounds well-known in the art. Preferred are those compounds amenable to grafting or other methods of coating a solid substrate (e.g. dip coating, plasma polymerization, vapor deposition, stamp printing, gamma irradiation, electron beam exposure, thermal and photochemical radiation).

Generally, the backbone coating may be attached to the underlying substrate through either the active or passive constituent. In some embodiments, both constituents may engage in bonding interactions with the substrate.

The Active Constituent

The role of the active constituent is to provide a point for future diversity and would be represented by a functional group that is well known in the art to undergo a vast number of chemical transformations, such as an amine, hydroxyl, anhydride, ester, carboxylic acid, ketone, epoxide, isocyanate and so on. Many well-known chemical monomers may be employed as active constituents in the formation of a synthon backbone coating. Selection of a particular set of active constituents may depend on the passive constituents selected and the desired chemistry for applying the backbone coating to the substrate.

Generally, the active constituent comprises a chemical moiety, or substituent group that may be chemically modified with a spacer compound (see described below).

For example, in an embodiment where gamma-initiated free-radical grafting is employed, one could employ any of the following monomers as the active constituent in the backbone coating: hydroxyethyl methacrylate, maleic anhydride, N-hydroxysuccinimide methacrylate ester, methacrylic acid, diacetone acrylamide, glycidyl methacrylate, PEG methacrylate.

In an alternative embodiment, more than one different active constituent may be present in the same backbone coating. For example, the coating may be made using a mixture of two active monomers. Once prepared, using well-known orthogonal approaches to chemical transformations, it is possible to differentially modify each of the different active constituents in the presence of the others, in a sequential and predetermined manner.

In preferred embodiments the active constituent comprises a chemical moiety, or substituent group that is amenable to surface grafting methods known in the art.

Table 1 below lists an exemplary selection of chemical monomers that may be used to provide the active constituents in the present invention. The compounds in this table are not intended to be limiting. Many common chemical variants of these compounds, as well as, other compounds not listed here but well-known in the art of surface modification may also be used.

Preferably, copolymer B comprises an active constituent A derived from the polymerised residue of maleic anhydride.

TABLE 1

| Selection of Active Constituents | | | | |
|---|---|---|---|---|
| ACTIVE | 1 | 2 | 3 | 4 |
| A | 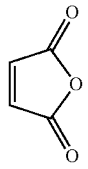 | 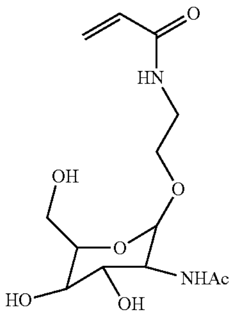 | 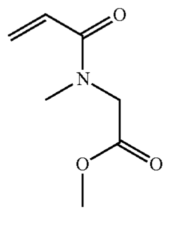 | 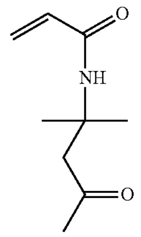 |

TABLE 1-continued

| Selection of Active Constituents | | | | |
|---|---|---|---|---|
| ACTIVE | 1 | 2 | 3 | 4 |
| B | 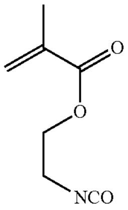 | 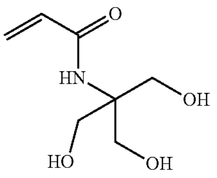 | 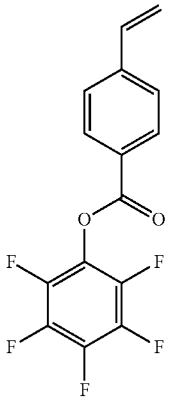 | 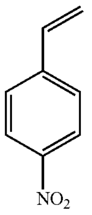 |
| C | 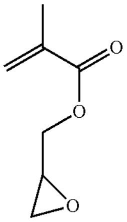 | 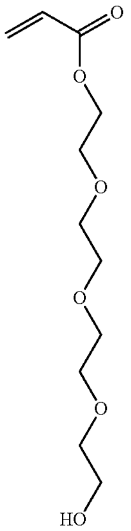 | 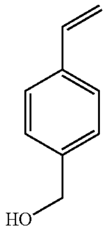 | 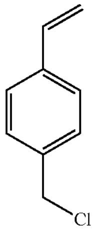 |
| D | 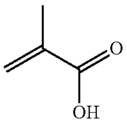 | 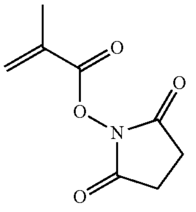 | 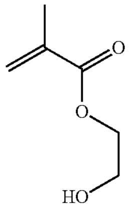 | 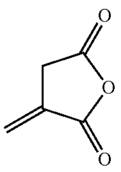 |

The Passive Constituent

Whereas the active constituent acts primarily as the point of attachment of the spacer, the primary role of the passive constituent is modification of molecular or macroscopic environment of the surface coating. For example, a set of passive constituents may be selected that modify the charge or the hydrophilicity of the surface coating. Modifications to passive constituents in a three dimensional stable network forming a surface coating allows determination of optimal surface properties for solid-phase applications. For example determination of a surface that allows binding of non-contiguous epitopes of a biomolecule so that they are available for a binding assay.

Further, the passive constituent also may act as a spacer unit for the active composition of the coating, in order to distribute the active group alternating, randomly, statistically or in a gradient fashion throughout the coating.

As mentioned above, in some embodiments the passive constituent may serve double-duty, also acting as a second active constituent for attachment of a spacer unit. Consequently, in some embodiments the passive constituent comprises a chemical moiety, or substituent group that may be chemically modified with a spacer compound. In this embodiment the reaction conditions for modification of the passive constituent are preferably orthogonal to those used to attach a spacer to the first active constituent.

The chemistry of the passive constituent may be provided by well known chemical monomers (preferably those that are commercially available) such as: styrene, dimethyl acrylamide, acrylonitrile, N,N dimethyl (or diethyl)ethyl methacrylate, 2-methacryloyloxy-ethyl-dimethyl-3-sulfopropyl-ammonium hydroxide, and methoxy PEG methacrylate. Preferably, copolymer B comprises a passive constituent B derived from the polymerised residue of styrene.

In preferred embodiments the passive constituent comprises a chemical moiety, or substituent group that is amenable to surface grafting methods known in the art.

Table 2 below lists a selection of chemical monomers that may be used to provide the passive constituents of the present invention. The compounds in this table are not intended to be limiting. Many common chemical variants of these compounds, as well as, other compounds not listed here but well-known in the art of surface modification may also be used.

TABLE 2

Selection of Passive Constituents

| Passive | 1 | 2 | 3 | 4 | 5 |
|---|---|---|---|---|---|
| A | 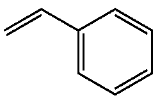 | 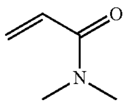 | 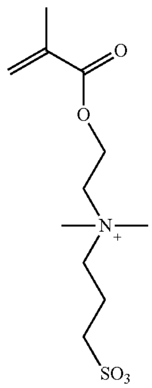 | 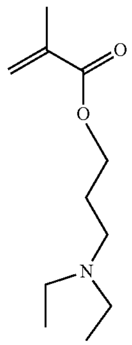 | 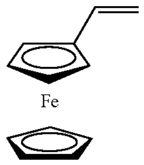 |
| B | 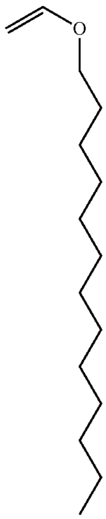 | 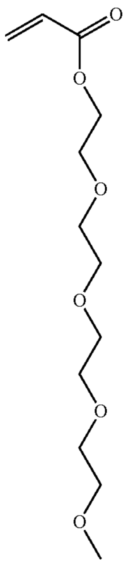 | 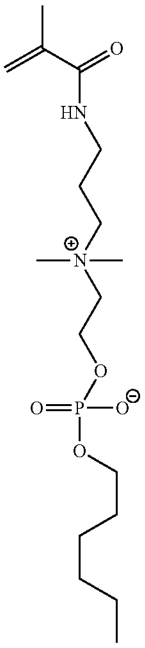 | 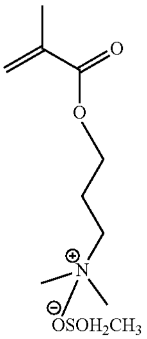 | 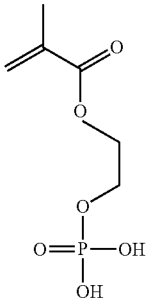 |

TABLE 2-continued

| Selection of Passive Constituents | | | | | |
|---|---|---|---|---|---|
| Passive | 1 | 2 | 3 | 4 | 5 |
| C | 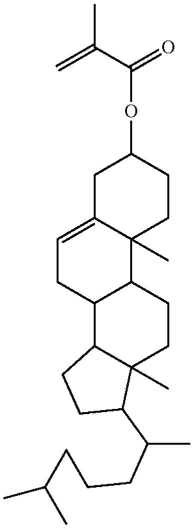 | 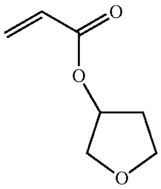 | 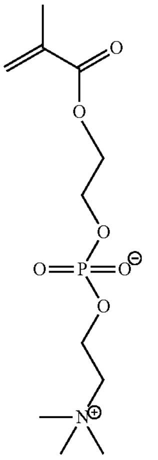 | 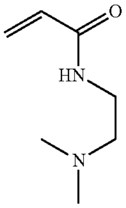 | 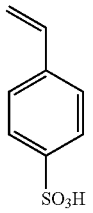 |
| D | 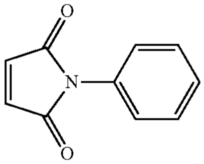 | 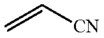 | 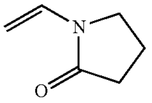 | 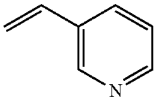 | 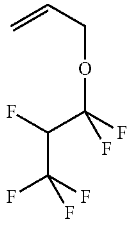 |

In an alternative embodiment, the desired macroscopic property of a surface coating for a selected solid phase application may be derived by in silico analysis of a range of synthon structures. Based on the in silico results, a passive constituent monomer with the chemical features necessary to generate the macroscopic property may be synthesized. Alternatively, the appropriate chemical features of the passive constituent may also be derived by in situ chemical transformation of an already applied backbone coating. In preferred embodiments, such in situ transformations of the passive backbone constituent are carried out in an orthogonal reaction scheme in order to maintain the integrity of the active constituent.

Application of the Backbone Coating

Generally, the synthon backbone coating may be applied to the substrate using any of the vast assortment of surface modifications methods present in the art (e.g. dip coating, plasma polymerization, vapor deposition, stamp printing, gamma irradiation, electron beam exposure, thermal and photochemical radiation).

In one embodiment, the backbone coating is polymerized from the constituent monomers on the solid substrate using chemistry well-known in the art. A wide range of polymerization processes present in the art may be utilized. For example, controlled and/or living polymerization techniques of cationic, anionic, radical (such as NMP, ATP, ATRP, RAFT, Iniferter), condensation, and metathesis (such as ROMP and ADMET) all may be used. Non-controlled methods of polymerization well known in the art may also be utilized with this invention.

In one preferred embodiment, the backbone coating may be provided by methods known to afford living polymerization. By definition, the end groups of such living polymers have the ability to be further transformed, either by addition of a monomer to extend the macromolecule with the same monomer, a mixture of monomers or new monomeric compositions. Also, the end groups may be modified using any of a variety of organic chemistry transformations well-known in the art of small molecule manipulation.

In embodiments where the synthon includes a control agent (C) end group on the backbone, living-controlled polymerization may be used to further modify the backbone coating. Control agents and methods of conducting living-controlled polymerization are well-known in the art. Methods of living-controlled polymerization and re-initiation on the surfaces of non-functionalized solid substrates is described in co-pending U.S. patent application Ser. No. 10/109,777 filed Mar. 28, 2002. Also, see, e.g. Canadian Patent applications 2,341,387 and 2,249,955 which disclose methods of living-controlled polymerization on solid polymer substrates.

Alternatively, the backbone coating may be applied to the substrate as a polymer solution, comprising macromers that will allow tethering by complementary chemistry to the surface of the substrate or encourage entanglement of the polymer in solution with the substrate. In the case of a macromer solution, the reactive units of the macromer may either be present at the end groups, or spaced throughout the backbone of the macromer in a random, block, or gradient fashion.

Preferably, the backbone coating is polymerised from constituent monomers to provide an alternating or block copolymer. The alternating, or substantially alternating character, of the copolymer is believed to provide an important spatial arrangement of the passive and active constituents which facilitates good surface coating of the substrate. Those skilled in the art will understand the degree of regularity necessary in order for a copolymer to be considered of alternating character. It is preferred that the alternating copolymer has an alternating character defined by greater than 70% of consecutive comonomer residue units being alternate between residues of the first comonomer and the second comonomer, more preferably greater than 90%. The block nature of the copolymer may also vary in an alternating fashion.

Preferably, the backbone coating is a copolymer of maleic anhydride and styrene.

The Spacer

The spacer group provides a synthetic "handle" by which functional groups may be attached to the active constituent of the backbone coating.

As used herein, the term "spacer," "spacer molecule" and "spacer unit" are used interchangeably. As used herein, the term "functional tether" is used to refer to the combined moiety of a spacer molecule modified with the desired functional group for the synthon.

Figure 2:
FIG. 2. The spacer molecule may be represented by the generic structure shown in the Figure.

In one preferred embodiment, the spacer molecule may be represented by the generic structure shown in FIG. 2:

Generally, both X and Y comprise chemical moieties or substituent groups that may be chemically modified independently, sequentially or under orthogonal conditions. For example, X may chemically react with the active constituent A to attach the spacer to the backbone. Subsequently, Y may be chemically modified with a desired functional group F.

Typical species may include for example, spacer molecules wherein X is the residue of an amino, hydroxyl, thiol, carboxylic acid, anhydrides, isocyanate, sulfonyl chloride, sulfonic anhydride, chloroformate, ketone, or aldehyde; Y is the same as defined for X; and Q is a linear or branched divalent organic group; and X and Y are not reactive with each other or Q. Preferably Q is selected from optionally substituted $C_1$ to $C_{20}$ alkylene, optionally substituted $C_2$ to $C_{20}$ alkenylene, optionally substituted $C_3$ to $C_{20}$ cycloalkylene, optionally substituted $C_2$ to $C_{20}$ alkynylene and optionally substituted $C_6$ to $C_{20}$ arylene, wherein one or more carbon atoms may be substituted with a heteroatom selected from O, S or N.

By "optionally substituted" is meant that a group may or may not be further substituted with one or more groups selected from, but not limited to, alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, acetyleno, carboximidyl, haloaryloxy, isocyano, cyano, formyl, carboxyl, nitro, nitroalkyl, nitroalkenyl, nitroalkynyl, nitroaryl, alkylamino, dialkylamino, alkenylamino, alkynylamino, arylamino, diarylamino, benzylamino, imino, alkylimine, alkenylimine, alkynylimino, arylimino, benzylimino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphonyl, arylsulphonyl, alkylsolphinyl, arylsulphinyl, carboalkoxy, alkylthio, benzylthio, acylthio, sulphonamido, sulfanyl, sulfo and phosphorus-containing groups, alkoxysilyl, silyl, alkylsilyl, alkylalkoxysilyl, phenoxysilyl, alkylphenoxysilyl, alkoxyphenoxysilyl, arylphenoxysilyl, allophanyl, guanidino, hydantoyl, ureido, and ureylene. A carbon atom is considered to be substituted if it has a double bond to a heteroatom, such as oxygen, sulfur or nitrogen to form a carbonyl, thiocarbonyl or imine group, respectively.

In the above definitions the terms "aryl" and "heteroaryl" refer to any substituent which includes or consists of one or more aromatic or heteroaromatic ring respectively, and which is attached via a ring atom. The rings may be mono or polycyclic ring systems, although mono or bicyclic 5 or 6 membered rings are preferred. Examples of suitable rings include but are not limited to benzene, biphenyl, terphenyl, quaterphenyl, naphthalene, tetrahydronaphthalene, 1-benzylnaphthalene, anthracene, dihydroanthracene, benzanthracene, dibenzanthracene, phenanthracene, perylene, pyridine, 4-phenylpyridine, 3-phenylpyridine, thiophene, benzothiophene, naphthothiophene, thianthrene, furan, benzofuran, pyrene, isobenzofuran, chromene, xanthene, phenoxathiin, pyrrole, imidazole, pyrazole, pyrazine, pyrimidine, pyridazine, indole, indolizine, isoindole, purine, quinoline, isoquinoline, phthalazine, quinoxaline, quinazoline, pteridine, carbazole, carboline, phenanthridine, acridine, phenanthroline, phenazine, isothiazole, isooxazole, phenoxazine and the like, each of which may be optionally substituted.

In the above definitions, the term "alkyl", used either alone or in compound words such as "alkenyloxyalkyl", "alkylthio", "alkylamino" and "dialkylamino" denotes straight chain, branched or cyclic alkyl, preferably $C_{1-10}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

In the above definitions the term "alkoxy" denotes straight chain or branched alkoxy, preferably $C_{1-10}$ alkoxy. Examples of alkoxy include methoxy, ethoxy, n-propoxy, isopropoxy and the different butoxy isomers.

The term "alkenyl" denotes groups formed from straight chain, branched or cyclic alkenes including ethylenically mono-, di- or poly-unsaturated alkyl or cycloalkyl groups as previously defined, preferably $C_{2-10}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

The term "alkynyl" denotes groups formed from straight chain, branched or cyclic alkyne including those structurally similar to the alkyl and cycloalkyl groups as previously defined, preferably $C_{2-10}$ alkynyl. Examples of alkynyl include ethynyl, 2-propynyl and 2- or 3-butynyl.

The term "acyl" either alone or in compound words such as "acyloxy", "acylthio", "acylamino" or "diacylamino" denotes carbamoyl, aliphatic acyl group and acyl group containing an aromatic ring, which is referred to as aromatic acyl or a heterocyclic ring which is referred to as heterocyclic acyl, preferably $C_{1-10}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

In alternative embodiments, the spacer molecule may have a branched structure whereby multiple functional groups may be attached at the ends of the branches.

Generally, there are two ways in which the spacer S may be incorporated into the synthon:

(1) A spacer molecule with a desired functional group already attached to at least one end is chemically coupled to the backbone.

(2) A spacer molecule is attached to the active constituent. Then in a separate synthetic step, the spacer molecule is further modified to attach a desired functional group.

In some embodiments, a spacer molecule may be attached, then modified with more than one functional group.

In one embodiment the spacer molecule is a linear chain molecule and a functional tether is formed by modifying the end of the chain distal from the site of attachment to the active constituent of the synthon.

By modifying the chemical or structural properties of the spacer molecule it is possible to generate synthons with a range of macroscopic coating properties. For example, glycol oligomer chains provide a relatively rigid linear structure, whereas simple hydrocarbons adopt more folded conformations. These differences in spacer geometry also may vary with chain length or the presence of charged groups in the spacer molecule. These differences in geometry provided by the spacer molecule properties directly affects the orientation of the functional group with respect to the backbone and thereby affects the overall macroscopic properties of the surface coating. Modification of these properties may greatly affect the complementary or antagonistic interactions between the surface and a biomolecule, cell or other chemical entity immobilized thereon.

Figure 3:
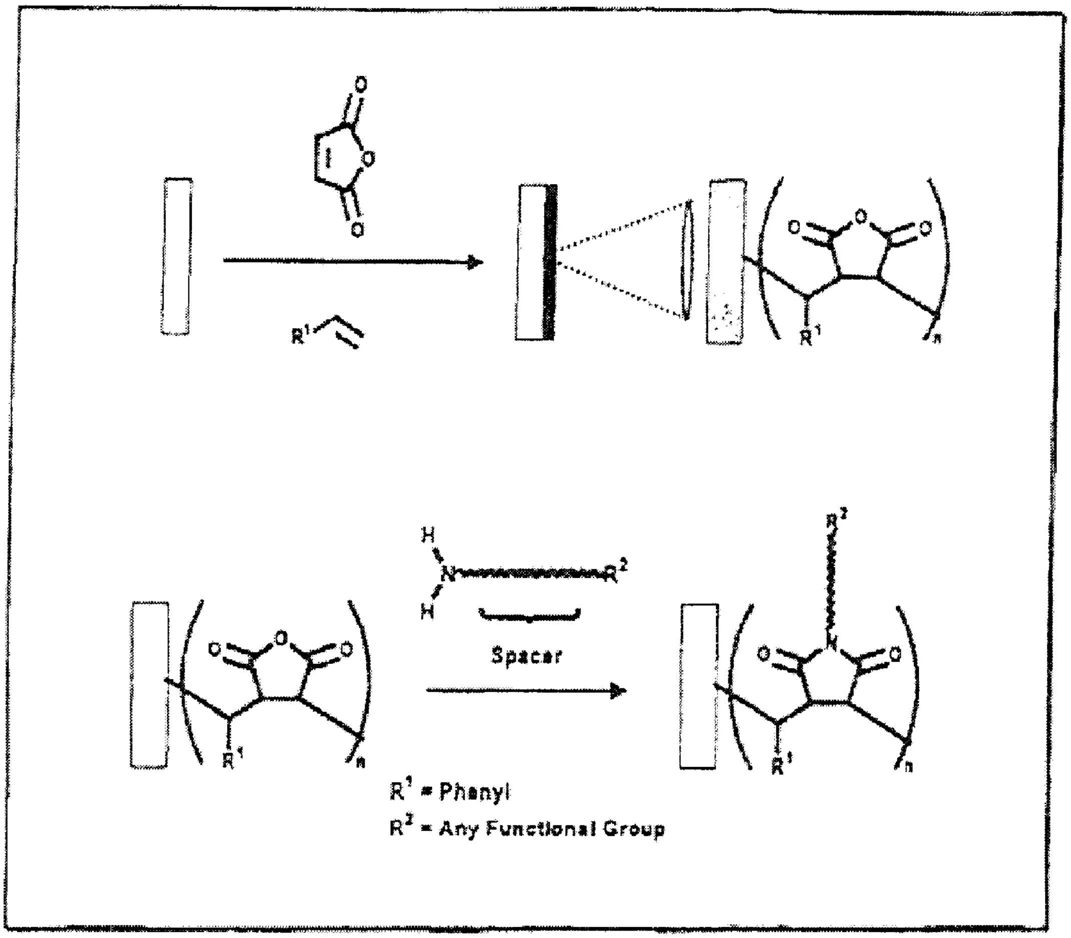
FIG. 3 illustrates the formation of a backbone coating on a substrate and subsequent attachment of a spacer.

In FIG. 3, the backbone coating is applied by polymerization of the active constituent, maleic anhydride, and the passive constituent, styrene. The spacer unit features an amine at one end that forms a covalent linkage to the active constituent resulting in a maleimide.

Preferably the spacer unit is a residue of a diamine, more preferably an alkyl diamine. It is particularly preferred that the spacer unit S is a residue of 1.5-diaminopentane or N-(3-aminopropyl)-1,3-propanediamine.

The Functional Group

The functional group may serve different roles in various embodiments. For example, the functional group may act as a site for further chemical modification of the surface. In the instance, where the functional group is capped with a polymerization initiator, the possibility exists to add another level of synthon diversity.

Figure 4:
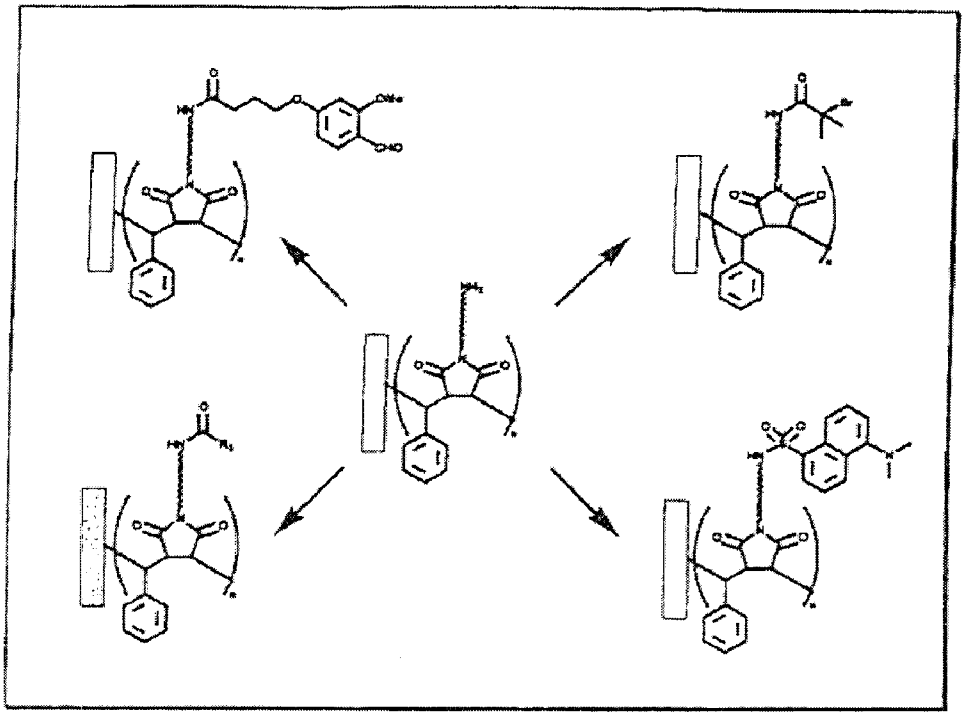
FIG. 4 shows a spacer with an amine moiety provides the site for chemical modification with four different functional groups thereby resulting in four different, but related synthon surface coatings.

In FIG. 4, a spacer with an amine moiety provides the site for chemical modification with four different functional groups thereby resulting in four different, but related synthon surface coatings.

Preferably, the functional group F is a group capable of binding or chemically reacting with a biological molecule or component. The functional group F also preferably comprises a primary or secondary amine group.

Screening for Surface Optimization

In FIG. 4, the functional group on each of the four coatings may serve as the primary site for a complementary binding interaction. By screening the four coatings in a desired solid phase binding assay, one may determine which surface is optimal. Subsequently, based on the best of the four synthons shown in FIG. 4, new libraries of related synthons may be generated to further optimize the surface for the desired application in an iterative fashion. For example, the next iteration may vary only the spacer length. Hence, synthons may be generated with functional groups exhibiting a range of molecular diversity in order to find the optimal surface for binding a complementary molecular species such as a receptor or other large biomolecule. For example, a library of synthons may be generated comprising a range of functional groups in order to find the optimal surface coating for binding the β-adrenergic receptor in a surface plasmon resonance experiment.

High-Throughput Advantage

Moreover, FIG. 4 illustrates the high-throughput advantage afforded by some embodiments of the synthon-based approached. As mentioned in the Background of the Invention, generation of surface diversity on solid phases has been limited by the difficulty of developing chemical methods for grafting new coatings onto solid substrates. Prior methods have focused on utilizing solution reactions to generate a diverse library of candidate compounds for coating a substrate. These methods have encountered a bottleneck in getting the solution-phase compounds coated onto a solid-phase substrate. This bottleneck results from the general lack of development of the science of grafting materials onto solids to form coatings.

As shown in FIG. 4, the present invention provides a high-throughput solution to generating surface diversity by avoiding this bottleneck. Instead, in preferred embodiments, libraries of diverse surfaces may be generated from a single backbone coating applied by a well-characterized grafting procedure. Subsequently, diversity may be introduced to the solid phase surface in a combinatorial manner by varying the spacer and functional groups structures through well-known synthetic routes.

Figure 5:
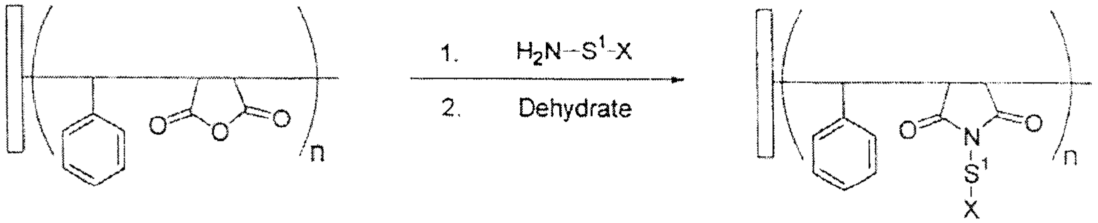
FIGS. 5 and 6 show that when $H_2N—S_1—X$ is a symmetrical diamine such as $H_2N—(CH_2)_6—NH_2$, a large number of functional groups with a range of functional and molecular diversity may be added.
Figure 6:
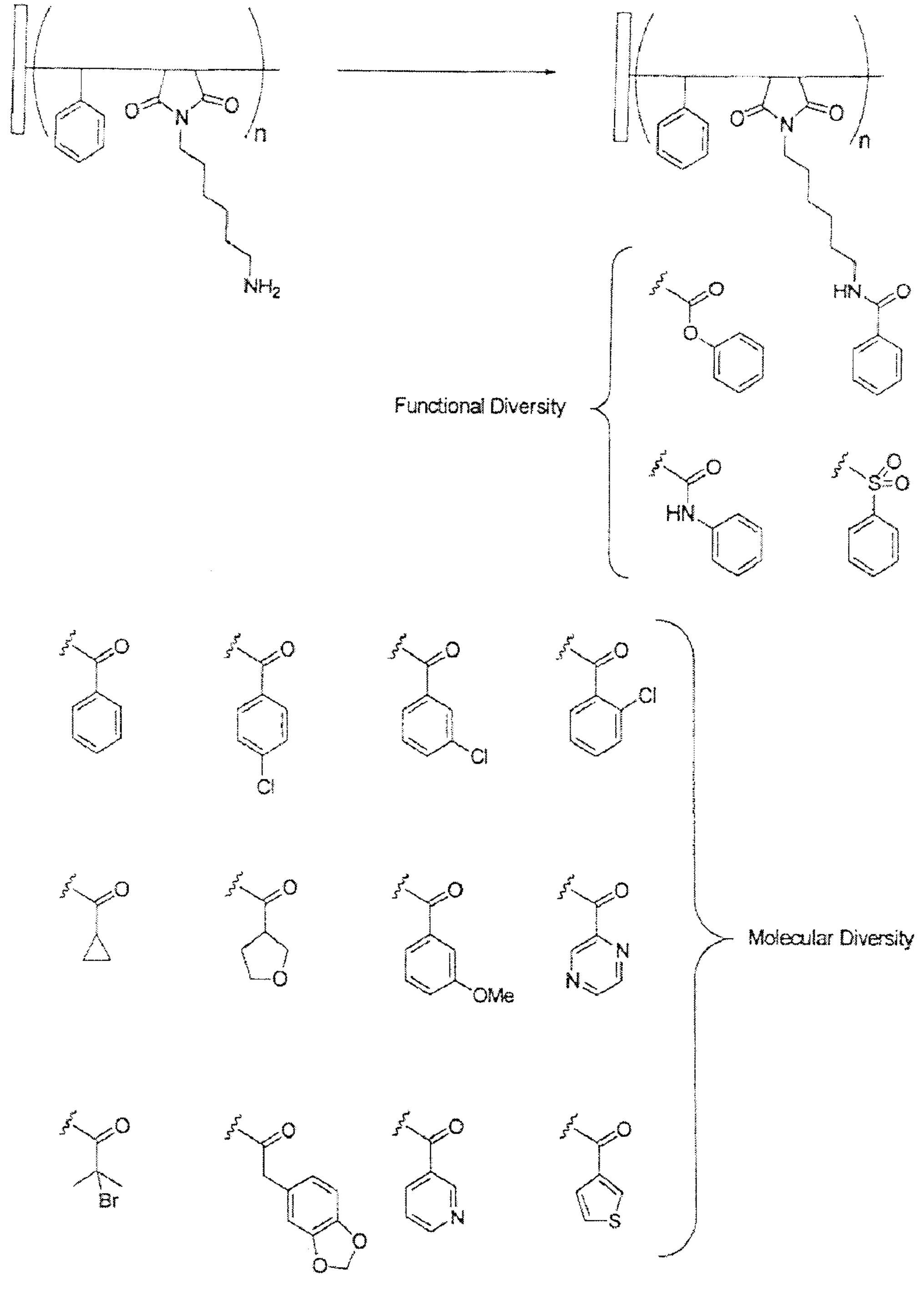

High-throughput generation of molecular diversity for detecting complementary binding interactions, as well as, for further chemical modification may be achieved by modifying the functional group on a relatively simple synthon backbone-spacer configuration. As shown in FIGS. 5 and 6, when $H_2N—S_1—X$ is a symmetrical diamine such as $H_2N—(CH_2)_6—NH_2$, a large number of functional groups with a range of functional and molecular diversity may be added.

Incorporation of Grafting and Polymerization Methods

In a preferred embodiment, the synthon-based approach to generation of diverse surface coatings may be carried out using well-known or readily-constructed free radical polymerization technology. This embodiment is particularly well-suited to generating synthon surface coatings on polymeric substrates such as polyolefins. In preferred embodiments, the polymeric substrate such as polypropylene or, may be already be coated with sytreneic, (meth)acrylic, (meth)acrylamides, or other related graft coatings. The manner by which this initial coating is a generated is well known in the art, gamma grafting, whereby the initiation requirements for the graft polymerisation to occur is from a cobalt-60 source, or the like.

The Substrate

The combinatorial advantages of the present synthon-based surface discovery system are independent of the nature of the base substrate material or how the synthon is applied to the surface. Hence surface diversity may be explored across a wide range of substrates. The substrate used in accordance with present invention is generally a solid and provides an integral surface or plurality of surfaces upon which the different surface coating(s) may be applied. Preferably, the substrate is selected from glass, silicon, metals, and organic polymers, other synthetic or natural materials, and combinations thereof.

The substrate may for example be provided in the form of a microscope slide, microtitre plate, porous membrane, pipette tip, tube or a plurality of beads.

Preferably, the substrate is an organic polymer. Suitable organic polymers include, but are not limited to, polytetrafluoroethylene, polystyrene, polypropylene, polyethylene, polyvinylidenefluoride and polymethylmethacrylate.

Further, the substrate may be porous, non-porous, and/or any geometric shape, e.g. bead, or flat. A variety of porous polymeric substrates with co-continuous architecture useful with the present invention are described in co-pending U.S. patent application Ser. No. 10/052,907 filed Jan. 17, 2002, which is hereby incorporated by reference herein.

In a preferred embodiment of the invention the substrate is an organic polymer in the form of a plurality of beads. Preferably, the beads are labelled such that a particular coating can be related to a particular bead or subgroup of beads. Suitable polymeric beads for use as a substrate in accordance with the present invention include, but is not limited to, Luminex™ beads.

Multiplexed Applications

The present compositions and methods allow surface diversity to be explored in a high-throughput fashion by, for example, building different synthons in an array format on a single substrate. A variety of multiplex formats such as arrays or beads may be used. For example, a single synthon backbone coating may be applied across the full substrate surface. Then different spacer units or functional group variants may be generated in different localized regions on the substrate.

As used herein, a "region" of a substrate includes a point, area or other location on the surface of the substrate. Each different surface coated on the substrate occupies discrete regions on the substrate.

In one preferred embodiment, photolithographic or micromirror methods may be used to spatially direct light-induced chemical modifications of spacer units or functional groups resulting in attachment at specific localized regions on the surface of the substrate. Light-directed methods of controlling reactivity and immobilizing chemical compounds on solid substrates are well-known in the art and described in U.S. Pat. Nos. 4,562,157, 5,143,854, 5,556,961, 5,968,740, and 6,153,744, and PCT publication WO 99/42813, each of which is hereby incorporated by reference herein.

Alternatively, plural localized synthon generation on a single substrate may be achieve by precise deposition of chemical reagents. Methods for achieving high spatial resolution in depositing small volumes of a liquid reagent on a solid substrate are disclosed in U.S. Pat. Nos. 5,474,796 and 5,807,522, both of which are hereby incorporated by reference herein.

The term "array" may or may not require the identification of each different surface coating in terms of co-ordinates for its location. An array may be in a pattern or be random and may comprise two or more coatings, or the same coating in different regions on the same substrate. The underlying substrate may be uniform in its ability to accept a surface coating. Or the substrate may have regions with different abilities to bind specific surface coatings resulting in a spatial pattern depending on the coating.

Screening of Diverse Surface Environments

Figure 7:
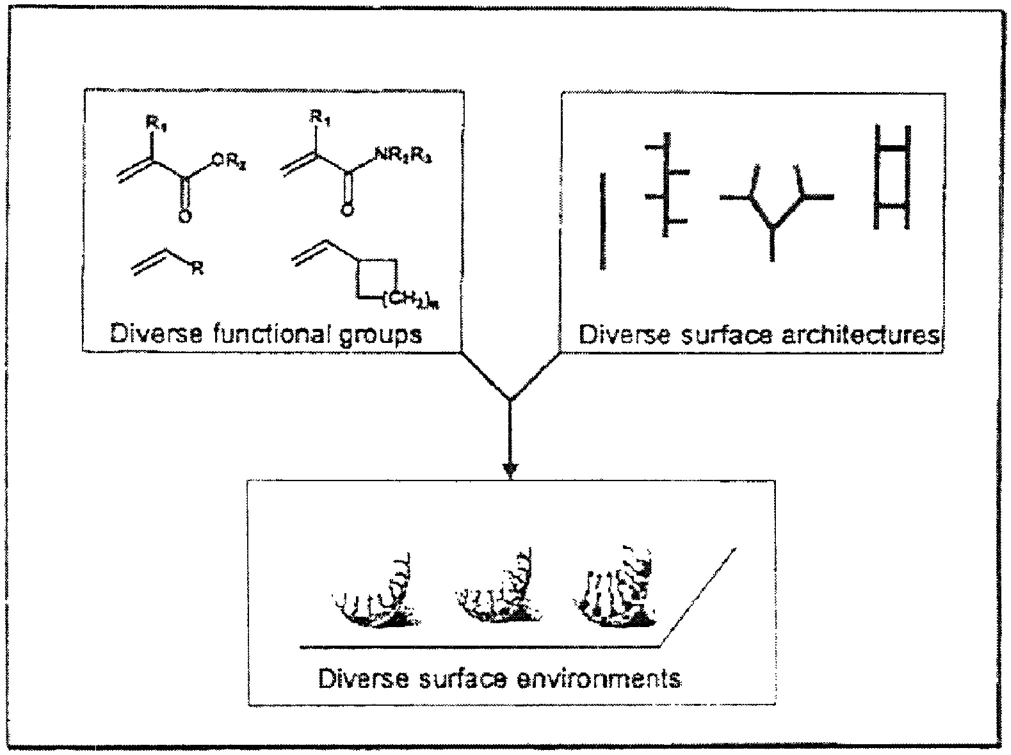
FIG. 7. The generation of a combinatorial selection of surface coatings provides a spectrum of molecular and macroscopic surface properties.

Surface coatings prepared using the synthon-based approach of the present invention may find use in a wide range of solid phase applications. The generation of a combinatorial selection of surface coatings provides a spectrum of molecular and macroscopic surface properties. The method provides a diversity of surface environments as shown in FIG. 7.

Each of these surfaces may potentially create an optimum environment or have optimal properties for a particular solid phase application. However, the greater the number of diverse surfaces in a library requires more screening for each particular application.

Generally, the surface coatings of the present invention may be screened for optimal performance in a solid phase application of interest by methods well known in the art. For example, such screening may involve detecting specific binding of cells to the surface and consequently may utilize flow cytometry as, for example, described by Needels et al. (1993).

Other screening methods useful with the present invention include any of the great number of isotopic and non-isotopic labeling and detection methods well-known in the chemical and biochemical assay art. For example, a library of surface coatings of the present invention may be screened for the ability to bind a specific peptide in an active configuration on the surface. An active configuration refers to an orientation of the molecule on the surface coating whereby the molecule may be specifically detected with a selected probe molecule, e.g. a fluorescently coupled antibody that specifically binds the molecule.

Alternatively, spectroscopic methods well-known in the art may be used to determine directly whether a molecule is bound to a surface coating in an desired configuration. Spectroscopic methods include e.g., UV-VIS, NMR, EPR, IR, Raman, mass spectrometry and other methods adapted to surface analysis well-known in the art.

Examples of biological compounds that may be screened for binding in the proper configuration on surface coating generated by the synthon-based approach of the present invention include, e.g. agonists and antagonists for cell membrane receptors, toxins, venoms, viral epitopes, hormones, sugars, cofactors, peptides, enzyme substrates, drugs inclusive of opiates and steroids, proteins including antibodies, monoclonal antibodies, antisera reactive with specific antigenic determinants, nucleic acids, lectins, polysaccharides, cellular membranes and organelles.

In addition, the present invention may be employed to generate optimal surface coatings for immobilized nucleic acids. These coatings may be used in any of a large number of well-known hybridization assays where nucleic acids are immobilized on a surface of a substrate, e.g. genotyping, polymorphism detection, gene expression analysis, fingerprinting, and other methods of DNA- or RNA-based sample analysis or diagnosis.

Various aspects of the present invention may be conducted in an automated or semi-automated manner, generally with the assistance of well-known data processing methods. Computer programs and other data processing methods well known in the art may be used to store information including e.g. surface coating library chemical and macroscopic properties. Data processing methods well known in the art may be used to read input data covering the desired characteristics.

Alternatively, or in addition, data processing methods well known in the art may be used to control the processes involved in the present invention, including e.g applying or polymerizing the backbone coating on the substrate; control of chemical reactions involved in further generating the synthon; and/or the reactions and interactions occurring in, within or between a population or array of surface coatings on a substrate.

The invention will now be described with reference to non-limiting examples. However it is to be understood that the particularity of the following description of the invention is not to supersede the generality of the invention previously described.

EXAMPLES

Figure 8:
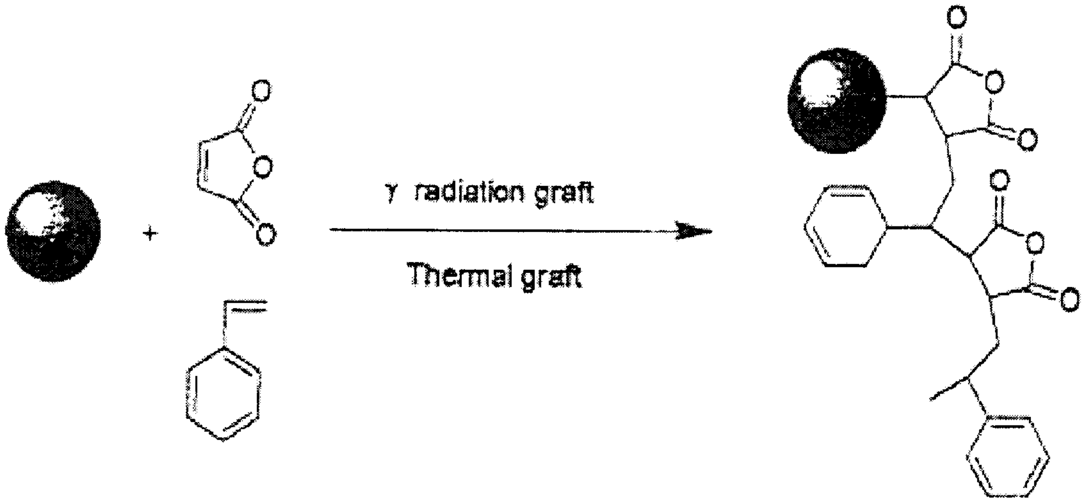
FIG. 8 illustrates the reaction carried out in generating the backbone coating.

1. Generation of a Maleic Anhydride (MAn)-Styrene Backbone Coating on a Polymeric Solid Substrate FIG. 8 illustrates the reaction carried out in generating the backbone coating. Plastic hollow cylinders, measuring 6 mm in length, 3 mm in diameter were pre-radiated in air at room temperature (1.8 KGy/h for 7 hours). A 40% (v/v) solution of styrene and maleic anhydride, present in mole equivalent proportions, in toluene was prepared and the added to the irradiated plastic cylinders. The mixture was then purge with nitrogen gas for 5 minutes via a septum and heated, with agitation at 60 C for 6 hours. The plastic cylinders were then isolated from the polymerised solution, washed thoroughly to remove non-grafted polymer and dried to constant weight.

Figure 9:
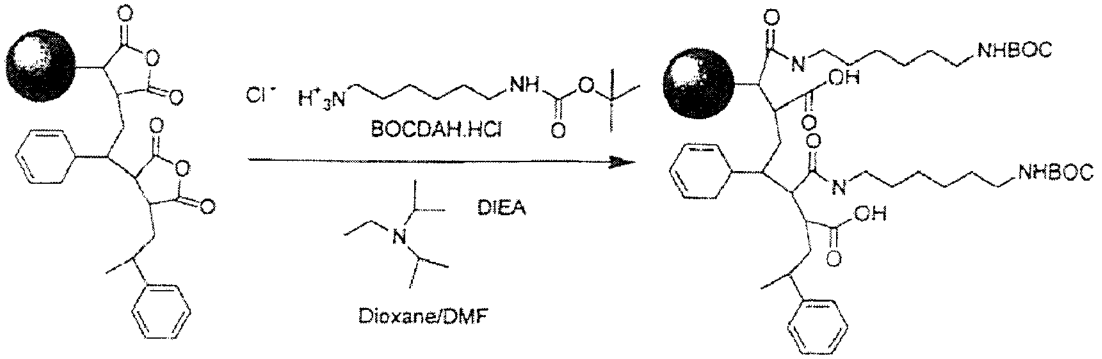
FIG. 9 shows Step 1: Ring Opening with Amines.

2. Attachment and Subsequent Deprotection of Tert-Butyl Carbamate (BOC) Protected Diamines Spacer Units to MAn-Sty Backbone Coating Step 1: Ring Opening with Amines (see FIG. 9)

A 1:1 DMF/Dioxane solution comprising an excess equivalents of the protected diamine was charged with plastic cylinders prepared above in example 1. A 6× excess DIEA was added to the solution and the solution left to react at 60 C for 2 hours, after which the plastic cylinders where isolated from the reaction mixture and washed thoroughly. Spectroscopic evidence (ATR and Raman) established the disappearance of the anhydride.

Figure 10:
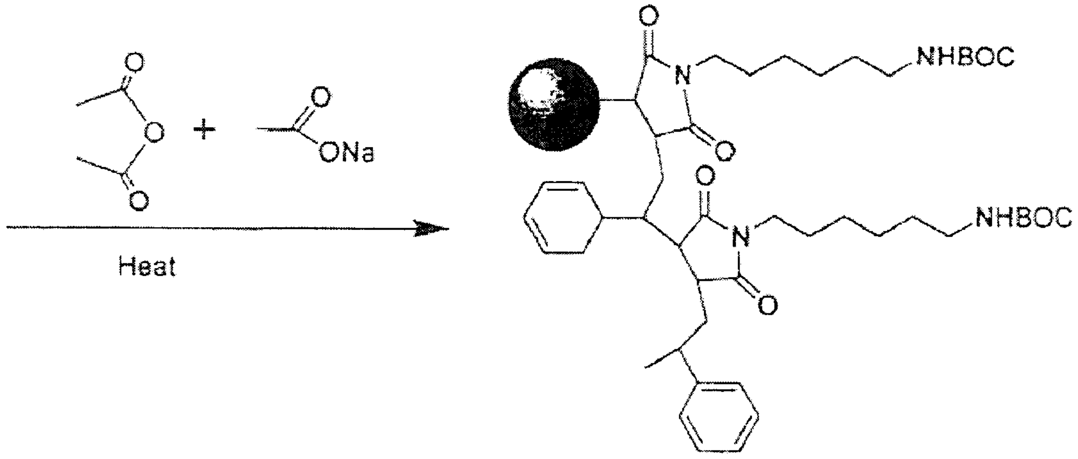
FIG. 10 shows Step 2: Ring Closure to the Imide.

Step 2: Ring Closure to the Imide (see FIG. 10)

The ring closure of the amic acid was effected by heating the material from step 1 of example 2 prepared above, at 60° C. in DMF in the presence of acetic anhydride and sodium acetate for 4 hours. The plastic cylinders were then washed extensively to afford the ring closed, grafted imide.

Figure 11:
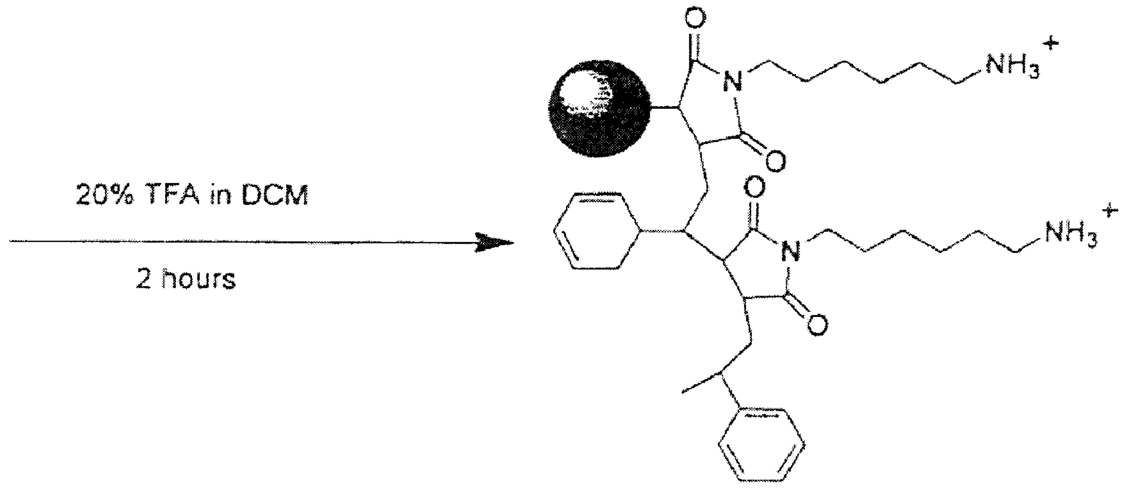
FIG. 11 show Step 3: Liberating the Amine.

Step 3: Liberating the Amine (see FIG. 11).

The removal of the amine protection group was performed under standard acid deprotection conditions by placing a sample of the plastic cylinders prepared above in example 2, step 2 were placed in a 20% Trifluoroacetic acid in dichloromethane for 2 hours. The deprotected, acidified samples were than washed extensively with dichloromethane prior to neutralization.

Figure 12:
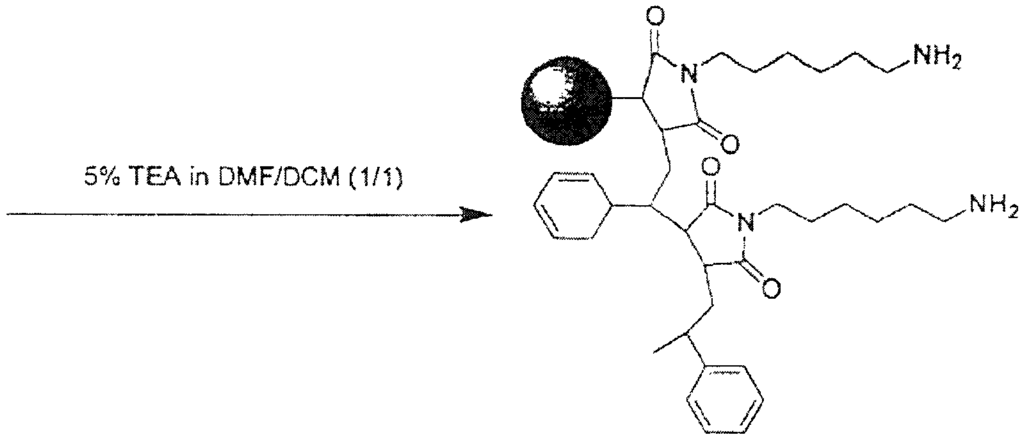
FIG. 12 shows Step 4: Neutralization of Grafted Amine.

Step 4: Neutralization of Grafted Amine (see FIG. 12)

The acidified samples prepared above in example 2, step 3 were treated with 5% triethyl amine in a 1:1 dimethyl formamide/dichloromethane, for 20 minutes, then washed extensively with dimethyl formamide and dichloromethane, prior to drying and determination of amine activity as described in Example 3, below.

3. Determination of Amine Activity

A sample of the grafted material prepared above in example 2, step 4, were treated with an excess of Fmoc-β-Ala-OH in dichloromethane, in the presence of diisopropyl carbodiimide. The Fmoc from the coupled Fmoc-β-Ala-OH to the pendant amine on the plastic cylinder was then cleaved by exposure of the plastic cylinders to a 20% solution piperidine in dimethyl formamide and the liberated Fmoc detected spectrophotometrically, to afford a concentration of active amines on the graft of 0.108 micromoles.

4. Synthon Coating: Disks Examples

I. Library of Maleimides

Step 1. Preparation of Maleic Anhydride/Styrene Graft Co-Polymer on PFA Disks.

Maleic anhydride/Styrene was covalently attached onto a tetrafluoroethylene-perfluoroalkyl-vinylether copolymer (PFA) disk using the γ-irradition technique. Three thousand PFA disks (6 mm diameter×0.8 mm thickness) were immersed in 150 mL 20% maleic anhydride in ethyl acetate (w/v) and 150 mL 20% styrene in ethyl acetate (v/v) containing 0.010 M HCl in dioxane in a 500 mL glass bottle. The solution was degassed by bubbling with $N_{2(g)}$ for 10 min. The glass bottle was sealed with a Teflon screw cap and γ-irradiated with a $^{60}Co$ source. The grafted disks were thoroughly washed with DMF and $CH_2Cl_2$ to remove residual monomer and non-grafted co-polymer and dried overnight under vacuum at 30° C. After drying, the disks were weighed to give an average mass change of 0.92% per disk (1.94 μg/$mm^2$).

Step 2: Reaction of Maleic Anhydride/Styrene Graft System with Primary Amines.

A 50 mL glass vial was charged with maleic anhydride/styrene grafted PFA disks (100 disks) and 20 mL of primary amine (1 M, Table 3) in DMF before the vial was sealed and shaken overnight. After 16 h, the solution was removed and the disks washed with DMF and $CH_2Cl_2$ before drying under vacuum to give the mixed (amide-carboxylic acid-phenyl) system.

TABLE 3

| List of Primary Amines for Disks | |
|---|---|
| No. | Amine |
| 1 | 2-(Aminomethyl)-18-crown-6 |
| 2 | 4-METHOXYPHENETHYLAMINE |
| 3 | Benzylamine |
| 4 | N-Acetylethylenediamine |
| 5 | Undecyclamine |
| 6 | 1-NAPHTHALENEMETHYLAMINE |
| 7 | 1-(2-AMINOETHYL)PYRROLIDINE |
| 8 | 2-(2-Aminoethoxy)ethanol |
| 9 | Tetrahydrofurfuryl amine |
| 10 | 2-(2-CHLOROPHENYL)ETHYLAMINE |
| 11 | Propylamine |
| 12 | 2-(aminomethyl)pyridine |
| 13 | 3,4-DIMETHOXYPHENETHYLAMINE |
| 14 | 3-PHENYL-1-PROPYLAMINE |
| 15 | 4-CHLOROBENZYLAMINE |
| 16 | 1-(2-AMINOETHYL)PIPERIDINE |
| 17 | 4-PHENYLBUTYLAMINE |
| 18 | 4-AMINO-1-BUTANOL |
| 19 | 4-FLUOROBENZYLAMINE |
| 20 | 6-AMINO-1-HEXANOL |
| 21 | DECYLAMINE |
| 22 | NONYLAMINE |
| 23 | Octylamine |
| 24 | VERATRYLAMINE |
| 25 | CYCLOHEXANEMETHYLAMINE |
| 26 | 5-AMINO-1-PENTANOL |
| 27 | ISOPentylamine |
| 28 | 1-(3-AMINOPROPYL)IMIDAZOLE |
| 29 | 2-Methoxyethylamine |
| 30 | Ethanol amine |
| 31 | 3-Aminopropionitrile |
| 32 | 3-Methoxypropylamine |
| 33 | 3-FLUOROBENZYLAMINE |
| 34 | 3,4,5-Trimethoxybenzylamine |
| 35 | 4-Methoxybenzylamine |
| 36 | 2-Amino-1-propene-1,1,3-tricarbonitrile |
| 37 | p-Aminophenyl-beta-D-glucopyranoside |
| 38 | D-Glucosamine hydrochloride |
| 39 | p-Aminophenyl-beta-D-galactopyranoside |
| 40 | Bis-homotris |
| 41 | 3-(Diethylamino)propylamine |
| 42 | 2-METHOXYBENZYLAMINE |
| 43 | Isobutylamine |
| 44 | BUTYLAMINE |
| 45 | 4-(TRIFLUOROMETHYL)BENZYLAMINE |
| 46 | 3,5-DIMETHOXYBENZYLAMINE |
| 47 | 3-FLUOROPHENETHYLAMINE |
| 48 | Pentylamine |

Step 3: Cyclization of Mixed System to Give Styrene/Maleimide Graft Co-Polymer.

Mixed amide-carboxylic acid-styrene PFA disks (50 disks) derived from primary amines were treated with toluene (50 mL), acetic anhydride (0.25 M), and sodium acetate (0.025 M) before heating to 80° C. overnight. After 16 h, the vial was drained of reagent and the disks washed with toluene, DMF, and then $CH_2Cl_2$ before drying under vacuum to afford the library of styrene/maleimide surfaces, generated from one initial surface. At each stage in the coating assembly, XPS and ATR spectra were acquired and indicated that each transformation had been performed. Further, the assembled library of maleimides on disks was screened against anti Rabbit IgG, and a spectrum of very low to very high protein bindings events were observed.

II. Library of Maleimides with Diamine Spacers and Capping Groups

Step 1. Preparation of Maleic Anhydride/Styrene Graft Co-Polymer on PFA Disks.

Maleic anhydride/Styrene was covalently attached onto a tetrafluoroethylene-perfluoroalkyl-vinylether copolymer (PFA) disk using the γ-irradition technique. Three thousand PFA disks (6 mm diameter×0.8 mm thickness) were immersed in 150 mL 20% maleic anhydride in ethyl acetate (w/v) and 150 mL 20% styrene in ethyl acetate (v/v) containing 0.010 M HCl in dioxane in a 500 mL glass bottle. The solution was degassed by bubbling with $N_{2(g)}$ for 10 min. The glass bottle was sealed with a Teflon screw cap and y-irradiated with a $^{60}$Co source. The grafted disks were thoroughly washed with DMF and $CH_2Cl_2$ to remove residual monomer and non-grafted co-polymer and dried overnight under vacuum at 30° C. After drying, the disks were weighed to give an average mass change of 0.92% per disk (1.94 μg/mm$^2$).

Step 2: Reaction of Maleic Anhydride/Styrene Graft System with Diamines on Disk.

1943 PFA discs grafted with maleic anhydride/styrene from Step 1 were then split into 29 batches of 67 discs. Each batch was treated with a different diamine (0.5 M in DMF) from Table 4 to give, after washing, 29 different mixed (amide-carboxylic acid-phenyl) intermediates containing free amines.

TABLE 4

| List of Diamine Spacers for Maleimide Library | |
|---|---|
| No. | Diamine |
| 1 | Ethylenediamine |
| 2 | 1,4-Diaminobutane |
| 3 | 1,12-Diaminododecane |
| 4 | 1,5-Diaminopentane |
| 5 | 1,3-Diaminopropane |
| 6 | Diethylenetriamine |
| 7 | Dipropylenetriamine |
| 8 | Tetraethylenepentamine |
| 9 | Triethylenetetramine |
| 10 | 1,3-Cyclohexanebis(methylamine) |
| 11 | 1,9-Diaminononane |
| 12 | 4,9-Dioxa-1,12-dodecanediamine |
| 13 | N,N'-Bis(3-aminopropyl)ethylenediamine |
| 14 | Bis(hexamethylene)triamine |
| 15 | Tris(2-aminoethyl)amine |
| 16 | Pentaethylenehexamine |
| 17 | 1,4-Bis(3-aminopropyl)piperazine |
| 18 | 2,2'-Oxybis(ethylamine) dihydrochloride |
| 19 | 3,3'-Diamino-N-methyldipropylamine |
| 20 | 2,2'-Dimethyl-1,3-diaminopropane |
| 21 | N,N'-Bis(2-aminoethyl)-1,3-propanediamine |
| 22 | 2,2'-(Ethylenedioxy)bis(ethylamine) |
| 23 | DAB((PA)4 Generation 1.0 |
| 24 | DAB((PA)4 Generation 2.0 |
| 25 | p-Xylylenediamine |
| 26 | O,O'-Bis(3-aminopropyl)polyethylenediamine |
| 27 | Polyethylenimine |
| 28 | 1,7-Diaminoheptane |
| 29 | 4,7,10-Trioxa-1,13-trideanediamine |

Step 3: Reaction of Mixed (Amide-Carboxylic Acid Phenyl) Amine Intermediates with Carboxylic Acids.

Each batch of diamines from step 2 was split into 67 different separate discs. Each disc was treated with a different carboxylic acid from Table 5 in a

TABLE 5

| List of Carboxylic Acid Capping Groups for Maleimide Library | |
|---|---|
| No. | Acid |
| 1 | BOC-3-(1-naphthyl)-L-alanine |
| 2 | N(alpha)-BOC-L-lysine (Fmoc) |
| 3 | D-Tyrosine |
| 4 | O-tert-Butyl-L-serine (Fmoc) |
| 5 | FMOC-L-glutamic acid 5-benzyl ester |
| 6 | D-Phenylalanine (BOC) |
| 7 | BOC-L-Tyrosine |
| 8 | L-Tyrosine (BOC) |
| 9 | N-Benzyloxycarbonyl-L-tyrosine |
| 10 | FMOC-L-Phenylalanine |
| 11 | N-(9-FLUORENYLMETHOXYCARBONYL)-L-PROLINE |
| 12 | N-alpha-Carbobenzyloxy-L-tryptophan |
| 13 | N-CBZ-L-METHIONINE |
| 14 | N-FMOC-(L-ALANINE-OH)-H2O |
| 15 | N-Carbobenzyloxy-L-proline |
| 16 | 2-(DIPHENYLPHOSPHINO)BENZOIC ACID |
| 17 | 1-Pyrenebutyric acid |
| 18 | (1S)-(−)-CAMPHANIC chloride |
| 19 | 2,3,4,5-Tetrafluorobenzoyl chloride |
| 20 | Docosanoic acid |
| 21 | 2,6-Difluorophenylacetic acid |
| 22 | Piperonyloyl chloride |
| 23 | 2,3,4-TRIHYDROXYBENZOIC ACID |
| 24 | Pentafluorobenzoyl chloride |
| 25 | 4-METHOXYCYCLOHEXANECARBOXYLIC ACID |
| 26 | 3-Iodo-4-methylbenzoic acid |
| 27 | 4-Octyloxybenzoic acid |
| 28 | Cyanoacetic acid |
| 29 | 2-METHYL-1-CYCLOHEXANECARBOXYLIC ACID |
| 30 | N-TRITYLGLYCINE |
| 31 | 3-Phenoxybenzoic acid |
| 32 | 3-Indolebutyric acid |
| 33 | 3,5-Diisopropylsalicylic acid |
| 34 | 4-Methylvaleric acid |
| 35 | 2-Norbornane acetic acid |
| 36 | 2,3,4-Trimethoxybenzoic acid |
| 37 | 2-HYDROXY-1-NAPHTHOIC ACID |
| 38 | 4-TERT-BUTYLCYCLOHEXANECARBOXYLIC ACID |
| 39 | 2-Thiopheneacetic acid |
| 40 | 2-Biphenylcarboxylic acid |
| 41 | 3,4-Diaminobenzoic acid |
| 42 | DIETHYLPHOSPHONOACETIC ACID |
| 43 | Flufenamic acid |
| 44 | TRIDECANOIC ACID |
| 45 | (1R,3R,4R,5R)-(−)-QUINIC ACID |
| 46 | 2,2-Bis(hydroxymethyl)propionic acid |
| 47 | p-Toloyl chloride |
| 48 | Propionic anhydride |
| 49 | 3-Mercaptopropionic acid |
| 50 | Gibberellic acid |
| 51 | Z-L-leucyl-L-alanine |
| 52 | R(+)-N-(alpha-Methylbenzyl)phthalic acid monoamide |
| 53 | (+)-mono-(1S)-Menthyl phthalate |
| 54 | R(−)-2-Oxothiazolidine-4-carboxylic acid |
| 55 | 9H-Fluorene-9-carboxylic acid |
| 56 | Orotic acid anhydrous |
| 57 | BOC-L-leucine |
| 58 | 15-Hydroxypentadecanoic acid |
| 59 | ACEMETACIN |
| 60 | N-T-BOC-S-TRITYL-L-CYSTEINE |
| 61 | URACIL-4-ACETIC ACID |
| 62 | (+/−)-4-METHYLOCTANOIC ACID |
| 63 | N-ALPHA-T-BOC-NEPSILON-CBZ-L-LYSINE |
| 64 | Indomethacin |

TABLE 5-continued

| List of Carboxylic Acid Capping Groups for Maleimide Library | |
|---|---|
| No. | Acid |
| 65 | N-BENZOYL-BETA-ALANINE |
| 66 | N-ACETYL-L-TRYPTOPHAN |
| 67 | MEFENAMIC ACID |

solution of DMF, 1-hydroxy-7-azabenztriazole (0.25 M), and diisopropylethylamine (0.5 M). The reaction was agitated overnight before washing with DMF and methylene chloride to remove excess reagent.

Step 4: Cyclization of Mixed System to Give Styrene/Maleimide Graft Co-Polymer.

Mixed amide-carboxylic acid-styrene PFA disks from step 3 (50 disks) were treated with acetic anhydride (0.25 M) and sodium acetate (0.025 M) in toluene before heating to 80° C. overnight. After 16 h, the vial was drained of reagent and the disks washed with toluene, DMF, and then $CH_2Cl_2$ before drying under vacuum to afford the library of styrene/maleimide surfaces, generated from one initial surface.

At each stage in the coating assembly, XPS and ATR spectra were acquired and indicated that each transformation had been performed. Further, the assemble library of maleimides with diamine spacers and dapping groups on disks was screened against anti Rabbit IgG, and a spectrum of very low to very high protein bindings were observed.

5. Synthon Coating: Microarray Examples

I. Library of Maleimides

Step 1. Preparation of Maleic Anhydride/Styrene Graft Co-Polymer on Microscope Slide.

A procedure for applying a Synthon Coating in a microarray format can be accomplished as follows: A microscope slide of dimensions 2.5×7.5×0.1 cm, prepared from the injection molding of tetrafluoroethylene-perfluoroalkyl-vinylether copolymer (PFA), can be masked to create an array of 16×250 urn circular spots. Treatment of the masked slide with heptane plasma (5 min, 20 W, $10^{-3}$ torr) followed by removal of the mask yields a PFA slide consisting of 16×250 um thinly coated heptane spots. UV irradiation of the slide in the presence of benzophenone (0.05 M) in methanol followed by simultaneous polymerization and grafting of maleic anhydride (1.75 M) and styrene (1.75 M) in ethyl acetate selectively derivatizes the heptane layer to give arrayed spots that are densely functionalised with anhydride groups.

Step 2: Reaction of Maleic Anhydride/Styrene Graft Slide with Primary Amines.

Primary amine containing compounds (0.5 M) dissolved in DMF readily attach to the surface upon robotic printing of nanoliter droplets to each spot via ring opening of the anhydride. Each spot of 3 slides from step 1 were treated with a different primary amine (Table 6) to give three microarrays of 16 different mixed (amide-carboxylic acid-phenyl) intermediates. The arrays were washed exhaustively with DMF, $CH_2Cl_2$, and 1% acetic acid in DMF before drying under vacuum.

TABLE 6

| List of Primary Amines for Microarray | |
|---|---|
| No. | Amine |
| 1 | 2-(Aminomethyl)-18-crown-6 |
| 2 | 4-METHOXYPHENETHYLAMINE |
| 3 | Benzylamine |
| 4 | N-Acetylethylenediamine |
| 5 | Undecyclamine |
| 6 | 1-NAPHTHALENEMETHYLAMINE |
| 7 | 1-(2-AMINOETHYL)PYRROLIDINE |
| 8 | 2-(2-Aminoethoxy)ethanol |
| 9 | Tetrahydrofurfuryl amine |
| 10 | 2-(2-CHLOROPHENYL)ETHYLAMINE |
| 11 | Propylamine |
| 12 | 2-(aminomethyl)pyridine |
| 13 | 3,4-DIMETHOXYPHENETHYLAMINE |
| 14 | 3-PHENYL-1-PROPYLAMINE |
| 15 | 4-CHLOROBENZYLAMINE |
| 16 | 1-(2-AMINOETHYL)PIPERIDINE |
| 17 | 4-PHENYLBUTYLAMINE |
| 18 | 4-AMINO-1-BUTANOL |
| 19 | 4-FLUOROBENZYLAMINE |
| 20 | 6-AMINO-1-HEXANOL |
| 21 | DECYLAMINE |
| 22 | NONYLAMINE |
| 23 | Octylamine |
| 24 | VERATRYLAMINE |
| 25 | CYCLOHEXANEMETHYLAMINE |
| 26 | 5-AMINO-1-PENTANOL |
| 27 | ISOPentylamine |
| 28 | 1-(3-AMINOPROPYL)IMIDAZOLE |
| 29 | 2-Methoxyethylamine |
| 30 | Ethanol amine |
| 31 | 3-Aminopropionitrile |
| 32 | 3-Methoxypropylamine |
| 33 | 3-FLUOROBENZYLAMINE |
| 34 | 3,4,5-Trimethoxybenzylamine |
| 35 | 4-Methoxybenzylamine |
| 36 | 2-Amino-1-propene-1,1,3-tricarbonitrile |
| 37 | p-Aminophenyl-beta-D-glucopyranoside |
| 38 | D-Glucosamine hydrochloride |
| 39 | p-Aminophenyl-beta-D-galactopyranoside |
| 40 | Bis-homotris |
| 41 | 3-(Diethylamino)propylamine |
| 42 | 2-METHOXYBENZYLAMINE |
| 43 | Isobutylamine |
| 44 | BUTYLAMINE |
| 45 | 4-(TRIFLUOROMETHYL)BENZYLAMINE |
| 46 | 3,5-DIMETHOXYBENZYLAMINE |
| 47 | 3-FLUOROPHENETHYLAMINE |
| 48 | Pentylamine |

Step 3: Cyclization of Mixed System to Give Styrene/Maleimide Graft Co-Polymer.

Subsequent dehydration of the entire array using acetic anhydride (0.25 M) and sodium acetate (0.025 M) at 80° C. in toluene gives arrays of 16 different surface bound maleimides/styrene co-polymers.

At each stage in the coating assembly, XPS and ATR spectra were acquired and indicated that each transformation had been performed. Further, the assemble library of maleimides on a microarray was screened against anti Rabbit IgG, and a spectrum of very low to very high protein bindings events were observed.

II. Library of Mixed (Amide-Carboxylic Acid-Phenyl) Systems from Secondary Amines on Microarray.

Step 1. Preparation of Maleic Anhydride/Styrene Graft Co-Polymer on Microscope Slide.

A procedure for applying a Synthon Coating in a microarray format can be accomplished as follows: A microscope slide of dimensions 2.5×7.5×0.1 cm, prepared from the injection molding of tetrafluoroethylene-perfluoroalkyl-vinylether copolymer (PFA), can be masked to create an array of 16×250 um circular spots. Treatment of the masked slide with heptane plasma (5 min, 20 W, $10^{-3}$ torr) followed by removal of the mask yields a PFA slide consisting of 16×250 um thinly coated heptane spots. UV irradiation of the slide in the presence of benzophenone (0.05 M) in methanol followed by simultaneous polymerization and grafting of maleic anhydride (1.75 M) and styrene (1.75 M) in ethyl acetate selectively derivatizes the heptane layer to give arrayed spots that are densely functionalised with anhydride groups.

Step 2: Reaction of Maleic Anhydride/Styrene Graft Slide with Secondary Amines.

A PFA slide grafted with 16 maleic anhydride/styrene spots was elaborated with 16 different secondary amines (0.5 M, Table 7) dissolved in DMF via robotic printing. Washing of the slide with dimethylformamide followed by 1% acetic acid in dimethylformamide gives 16×250 um different mixed (amide-carboxylic acid-styrene) spots on the PFA slide.

TABLE 7

| List of Secondary Amines for Microarray | |
|---|---|
| No. | Secondary Amine |
| 1 | Dimethylamine |
| 2 | 3,3-Iminodipropionitrile |
| 3 | Morpholine |
| 4 | Bis(2-methoxyethyl)amine |
| 5 | Piperidine |
| 6 | Diethyl amine |
| 7 | N-Benzylmethylamine |
| 8 | 1-Methylpiperazine |
| 9 | 4-Piperidinone monohydrate hydrochloride |
| 10 | 1-Acetylpiperazine |
| 11 | 1,2,3,4-Tetrahydroisoquinoline |
| 12 | Pyrrolidinone |
| 13 | N-Methylpropargyl amine |
| 14 | N,N,N'-Trimethylethylenedianine |
| 15 | Thiomorpholine |
| 16 | Nipecotamide |

At each stage in the coating assembly, XPS and ATR spectra were acquired and indicated that each transformation had been performed. Further, the assemble library of mixed (amide-carboxylic acid-phenyl) systems from secondary amines on microarray was screened against anti Rabbit IgG, and a spectrum of very low to very high protein bindings events were observed.

III. Library of Mixed (Amide-Amide-Phenyl) System on Microscope Slide

Step 1. Preparation of Maleic Anhydride/Styrene Graft Co-Polymer on Microscope Slide.

A procedure for applying a Synthon Coating in a microarray format can be accomplished as follows: A microscope slide of dimensions 2.5×7.5×0.1 cm, prepared from the injection molding of tetrafluoroethylene-perfluoroalkyl-vinylether copolymer (PFA), can be masked to create an array of 16×250 um circular spots. Treatment of the masked slide with heptane plasma (5 min, 20 W, $10^{-3}$ torr) followed by removal of the mask yields a PFA slide consisting of 16×250 um thinly coated heptane spots. UV irradiation of the slide in the presence of benzophenone (0.05 M) in methanol followed by simultaneous polymerization and grafting of maleic anhydride (1.75 M) and styrene (1.75 M) in ethyl acetate selectively derivatizes the heptane layer to give arrayed spots that are densely functionalised with anhydride groups.

Step 2: Reaction of Maleic Anhydride/Styrene Graft Slide with Secondary Amines.

A PFA slide grafted with 16 maleic anhydride/styrene spots was elaborated with 16 different secondary amines (0.5 M, Table 7 above) dissolved in DMF via robotic printing.

Washing of the slide with dimethylformamide followed by 1% acetic acid in dimethylformamide gives 16×250 urn different mixed (amide-carboxylic acid-styrene) spots on the PFA slide.

Step 3: Reaction of Mixed (Amide-Carboxylic Acid-Phenyl) System with Diamine.

Twenty-nine copies of the slide in step 2 were treated with DMAP (10 mol %), 1,3-diisopropyl carbodiimide (0.25 M), and N-hydroxysuccinimide (0.15M) in DMF. After washing with DMF, the slides were separated and each treated with a different diamine from Table 6 above. After several hours, the slides were washed with DMF and allowed to dry under vacuum to give microarrays of mixed (2°-Amide-1°-amide-phenyl)amine systems. Hence, all slides contain the same 16 secondary amines, one for each spot, but each slide contains a different diamine, wherein all spots on a given slide have the same diamine.

Step 4: Reaction of Mixed (2°-Amide-1°-Amide-Phenyl) Amine Intermediates with Carboxylic Acids.

The thirty slides from step 3 above were each treated with a solution of 3-iodo-4-methylbenzoic acid (0.25 M), 1-hydroxy-7-azabenztriazole (0.25 M), and diisopropylethylamine (0.5 M) in DMF. The reaction mixtures were agitated overnight before washing with DMF and methylene chloride to remove excess reagent. At each stage in the coating assembly, XPS and ATR spectra were acquired and indicated that each transformation had been performed. Further, the assemble library of mixed (amide-amide-phenyl) system on a microarray was screened against anti Rabbit IgG, and a spectrum of very low to very high protein bindings events were observed.

6. Synthon Coating: Carboxylated Polymer Bead Examples

Synthon Coating Polymer

Inhibitor free styrene (86.4 mmol), maleic anhydride (86.4 mmol), and initiator AIBN (0.1 mmol) were mixed together in 1,4-Dioxane (48 ml) in a polymerisation ampoule and sealed with a rubber septum. The solution was degassed by nitrogen sparging then allowed to polymerise at 60° C. in a temperature controlled oil bath. After an appropriate time interval the polymerisation was stopped by precipitatin into a 10-fold excess of methanol. The copolymer was collected by filtration and purified once by reprecipitation into methanol from DMF. The alternating copolymer was characterised my GPC: Mw=270 000.

0.5 grams of the afforded polymer was dispersed into 50 ml of Millipore water and hydrolyzed at 80° C. with shaking over 5 days to afford the Synthon Coating Polymer, that is employed in the bead and plate examples below.

A) Absorption of the Synthon Coating Polymer

Step 1: A 100 uL bead suspension of 5 micron, carboxylated was washed once with 2 mls of Millipore water. The suspension was spun down and the bead plug resuspended into 1 ml of a 1 wt % solution of PEI (Aldrich, 750K). The PEI was allowed to adsorb for 30 minutes with occasional gentle shaking and subsequently washed vigorously 3 times with Millipore water and spun down to a bead plug. The PEI coated beads were then resuspended in 1 ml of 1% hydrolysed Synthon Coating Polymer I (described above) and allowed to adsorb for 30 min with occasional gentle shaking. The beads were then washed 3 times with Millipore water with each washing step including 20 min of gentle shaking and spun down to a bead plug.

Step 2: To effect the next coating stage, the spun down bead plugs with the PEI and adsorbed Synthon Coating Polymer were resuspended into 1 ml of a 5 mg/ml EDC water solution and after 1 min, 25 uL of the 1.5 pentyl diamine was added. The samples were shaken briefly and the coupling reaction was allowed to proceed for 2 hrs with occasional gentle shaking. As the beads tended to clump during this process, they were redispersed with a short stints in the ultrasonic bath. The diamine coupled beads were then washed exhaustively with Millipore water 5 times and spun down to a bead plug. These amine modified beads were resuspended into 1 ml of water and 200 uL of the, 3-iodo-4-methyl-benzoic acid, sulfo-NHS ester (~10 mg/ml of DMF) was added. The reaction was left to proceed for 2 hrs and were then exhaustively washed 5 times with Millipore water. It should be noted that this modification can be effected by any number of diamines (or other multi-amine building block) and carboxylic acids, to allow the generation of libraries of modified encoded beads from the single Synthon Coating Polymer modified bead.

At each stage in the coating assembly, XPS spectra were acquired and indicated that each transformation had been performed. This process was performed on a number of beads sets from Bangs Laboratories (L020621N, L020325G& Dyed: L011009A) and Luminex (L100-C124-01), B) Covalent Attachment of the Synthon Coating Polymer Step 1: A 100 uL bead suspension of 5 micron, carboxylated was washed once with 2 mls of Millipore water. The suspension was spun down and the bead plug resuspended into 1 ml of a 1 wt % solution of PEI (Aldrich, 750K). The PEI was allowed to adsorb for 30 minutes with occasional gentle shaking and subsequently washed vigorously 3 times with Millipore water and spun down to a bead plug. The covalent attachment of the Synthon Coating Polymer to the PEI coated beads was performed by resuspending the PEI beads in 1 ml of 1% Synthon Coating Polymer (preparation described above) that had been activated with EDC, and the reaction allowed to proceed for 30 min with occasional gentle shaking. The beads were then washed 3 times with Millipore water with each washing step including 20 min of gentle shaking and spun down to a bead plug.

Step 2: To effect the next coating stage, the spun down bead plugs with the PEI and adsorbed Synthon Coating Polymer were resuspended into 1 ml of a 5 mg/ml EDC water solution and after 1 mM, 25 uL of the 1,5 pentyl diamine was added. The samples were shaken briefly and the coupling reaction was allowed to proceed for 2 hrs with occasional gentle shaking. As the beads tended to clump during this process, they were redispersed with a short stints in the ultrasonic bath. The diamine coupled beads were then washed exhaustively with Millipore water 5 times and spun down to a bead plug. These amine modified beads were resuspended into 1 ml of water and 200 uL of the, 3-iodo-4-methyl-benzoic acid, sulfo-NHS ester (~10 mg/ml of DMF) was added. The reaction was left to proceed for 2 hrs and were then exhaustively washed 5 times with Millipore water. It should be noted that this modification can be effected by any number of diamines (or other multi-amine building block) and carboxylic acids, to allow the generation of libraries of modified encoded beads from the single Synthon Coating Polymer modified bead.

At each stage in the coating assembly, XPS spectra were acquired and indicated that each transformation had been performed. This process was performed on a number of beads sets from Bangs Laboratories (L020621N, L020325G& Dyed: L011009A) and Luminex (L100-C124-01), C) Multiplex Bead Based Assay Encoded Carboxylated beads employed in the assay were acquired from Luminex, and treated with Step 1 of the Absorption of the Synthon Coating Polymer described above. $5.0\times10^6$ microspheres were transferred to a 15 mL microcentrifuge tube, spun down to a pellet and resuspended in 5 mL of 0.1M MES, pH 4.5 making sure to vortex and sonicate beads well.

0.2 nmol of capture oligo probes (2 mL of 1:10 of stock in dH20) was added to the beads, followed by a fresh aliquot of 10 mg/mL EDC in dH2O (2.5 mL). The reaction was allowed to proceed for 30 minutes at room temperature in the dark, prior to washing and charging the vessel with another fresh solution of 2.5 mL of EDC. This solution was also incubated for 30 minutes at room temperature in the dark, then washed with 1.0 mL of 0.02% Tween-20. The suspension was centrifuged for 1 minute to produce pellet and the supernatant carefully removed. The beads were then washed with 1.0 mL of 0.1% SDS, centrifuged for 1 minute to produce pellet and the supernatant carefully removed. The beads were then finally suspended in 100 mL of TE, at pH 8.0 and stored at 2-8° C. in complete darkness.

The coupled beads were then resuspended 1.5×TMAC buffer and distributed to a sample or background well on the PCR plate. The amplified biotinylated DNA was then added and TE, pH 8.0 added to make a total of 17 mL. The solutions were gently pipet up and down to mix. The samples were covered with plate sealer and place in thermocycler under a program that is set at 95° C. (denaturing step) for 5 minutes and then 52° C. (hybridization step) for 15 minutes. The plate was then spun ($^3$2250×g, 3 minutes) and the supernatant carefully removed, and the plate placed back into the PCR at 52° C. 75 mL of reporter solution was then added to each well, mixed gently and incubate at 52° C. for 5 minutes prior to analysis via a Luminex machine, to afford an improved signal to noise over the non-modified Encoded Carboxylated beads.

7. Coating of a Multi-Well Plate

A) Non-Reactive Microtitre Plate

Step 1: 200 uL of a 1 wt % PEI (Aldrich, 750K) was added to the wells of a 96 well microtitre plate (Maxisorp, Nunc) and allowed to stand at room temperature for 60 min. The wells were then washed 5 times with Millipore water. 200 uL of a 1 wt % Synthon Coating Polymer (preparation described above) was added to the wells and the interaction allowed to proceed for 60 min. The wells were then washed 5 times with Millipore water.

Step 2: 200 uL of a 5 vol % 1,5 pentyl diamine in 5 mg/ml EDC water solution was added to the wells and coupling allowed to proceed for 2 hrs, and then the wells were washed 5 times with Millipore water. 200 uL of a coupling solution comprising 5 mg/ml EDC and 5 mg/ml 3-iodo-4-methylbenzoic acid in DMSO was added to the wells and allowed to proceed for 2 hours after which the wells were washed twice with fresh DMSO then 5 times with Millipore water.

It should be noted that this modification can be effected by any number of diamines (or other multi-amine building block) and carboxylic acids, to allow the generation of libraries of modified microtitre plate wells from a single Synthon Coating Polymer modified bead.

At each stage in the coating assembly, XPS spectra were acquired and indicated that each transformation had been performed. The modified plates could then be employed in standard immunoassay protocols for ELISA and other diagnostic procedures B) Reactive Microtitre Plate Step 1: 200 uL of a 1 wt % Synthon Coating Polymer (preparation described above) was added to the wells NHS active plate, DNA-BIND (Corning) and ReactiBind plate (Piece) and the reaction allowed to proceed for 60 min. The wells were then washed 5 times with Millipore water.

Step 2: 200 uL of a 5 vol % 1.5 pentyl diamine in 5 mg/ml EDC water solution was added to the wells and coupling allowed to proceed for 2 hrs, and then the wells were washed 5 times with Millipore water. 200 uL of a coupling solution comprising 5 mg/ml EDC and 5 mg/ml 3-iodo-4-methylbenzoic acid in DMSO was added to the wells and allowed to proceed for 2 hours after which the wells were washed twice with fresh DMSO then 5 times with Millipore water.

It should be noted that this modification can be effected by any number of diamines (or other multi-amine building block) and carboxylic acids, to allow the generation of libraries of modified microtitre plate wells from a single Synthon Coating Polymer modified bead.

At each stage in the coating assembly, XPS spectra were acquired and indicated that each transformation had been performed. The modified plates could then be employed in standard immunoassay protocols for ELISA and other diagnostic procedures.

8. Coating of PVDF Membrane

Step 1: Activation of the Membrane with a Grafted Synthon Polymer

Four, 10×20 cm pieces of Immobilon-$P^{SQ}$ PVDF membrane (Millipore) were placed into a 700 ml beaker. The beaker was filled with a 1.5-Methyl acetate solution of 1:1 Styrene and Maleic anhydride, degassed by nitrogen purging and sealed. The solution was then irradiated in a gamma cell for 100 min. The irradiated membranes were removed from the polymerisation solution and washed with a large excess of ethyl acetate. Once washing was complete, the membranes were dried under high vacuum overnight and stored in a low humidity cupboard.

Step 2: Modification of the Membrane

A standard solution of the amine in THF (100 ml, 0.25 M, 0.025 mol) was prepared for each amine used. Grafted PVDF membranes were cut to a size of 10×10 cm, and placed in a large Petrie dish. The 100 ml amine solution was then carefully poured into the Petri dish, ensuring that the membrane was fully wet. The Petri dishes were then sealed with lids and allowed to agitate (very slowly) overnight at room temperature. The reaction solution was removed from the petri dish and the membranes washed with THF, dried under vacuum overnight and stored in the low humidity cupboard.

It should be noted that this modification can be effected by any number of amines (or other multi-amine building block) to allow the generation of libraries of modified PVDF membranes from a single grafted Synthon Polymer modified membrane.

At each stage in the coating assembly, XPS and ATR spectra were acquired and indicated that each transformation had been performed. The modified plates could then be employed in standard electroblotting protocols for western blotting applications to increase the amount of captured protein available for immunoassay.

9. Synthon Coating: Determining the Optimum Coating for a Desired Specific Application Step 1: Preparation of Library on Desired Format:

A library of different but related surfaces are assembled in the desired format (microarray, bead, plated, etc) for the application, employing the methods described above.

Step 2: Screening of the Assembled Library

The assembled libraries are screened against the desired target for the desired application such as a biological screen for kinases, Rabbit IgG, cytokines or a synthetic screen for reaction optimizations, or the like. The outcome from this screen would be to identify the optimum surface for the said desired application, in a rapid and cost effective manner.

If the desired level of signal is not attained from the first screen of the libraries, a second, more focused library is then assembled with the knowledge from the first and the screen repeated until the desired level of signal is obtained. More than one surface from each screen may afford a signal of the desired level.

Step 3: Generation of a Synthon coating for a Desired Specific Application.

Having determined the optimum surface for the desired application, the identified surface can then be assembled by any means required, that affords the surface in a timely and cost effective manner. Further, the outcomes of a number of screening events can be assembled onto one surface, such as a microarray, resulting in a multiplex platform having, or consisting of multiple elements or parts to do more than one experiment.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. The reference to any prior art in this specification is not, and should not be taken as, an acknowledgment or any form of suggestion that that prior art forms part of the common general knowledge in Australia.

Those skilled in the art will appreciate that the invention described herein is susceptible to variations and modifications other than those specifically described. It is to be understood that the invention includes all such variations and modifications which fall within its spirit and scope. The invention also includes all the steps, features, compositions and compounds referred to or indicated in this specification, individually or collectively, and any and all combinations of any two or more of said steps or features.

The invention claimed is:

1. A method of forming a library of surface coating synthons of formula B-S-F on a substrate, the method comprising:

a) providing a substrate;

b) applying compound B to the substrate thereby enabling compound B to attach to the substrate, wherein compound B is a copolymer of passive constituent P and active constituent A;

c) applying compound S to the substrate thereby enabling compound S to attach to constituent A of compound B, wherein compound S is a spacer unit; and d) applying compound F to the substrate thereby enabling compound F to attach to spacer unit S, wherein compound F is a compound in the form of a biological or chemical functional group;

wherein steps a) to d) result in the formation of a synthon of formula B-S-F on the substrate, and wherein steps b) to d) are performed such that each synthon formed on the substrate differs from other synthons on the substrate by having a combination selected from the group consisting of:

a combination of constituent P and constituent A that is not found in other synthons on the substrate;

a combination of constituent P and compound S that is not found in other synthons on the substrate;

a combination of compound S and constituent A that is not found on other synthons on the substrate;

a combination of compound F and constituent P that is not found in other synthons on the substrate;

a combination of compound F and constituent A that is not found in other synthons on the substrate;

and a combination of compound F and constituent S that is not found in other synthons on the substrate, thereby forming a library of surface coating synthons of formula B-S-F on the substrate.

2. The method according to claim 1, wherein the substrate is selected from an organic polymer, glass, silicon, metal and combinations thereof.

3. The method according to claim 2, wherein the substrate is an organic polymer.

4. The method according to claim 3, wherein the organic polymer is selected from polytetrafluoroethylene, polystyrene, polypropylene, polyethylene, polyvinylidenefluoride and polymethylmethacrylate.

5. The method according to claim 3, wherein the organic polymer is in the form of a plurality of beads.

6. The method according to claim 5, wherein the beads are labeled such that a particular coating can be related to a particular bead or subgroup of beads.

7. The method according to claim 1, wherein the substrate is in the form of a microscope slide, microtitre plate, porous membrane, pipette tip, tube or a plurality of beads.

8. The method according to claim 1, wherein the library comprises at least 10 different surface coatings.

9. The method according to claim 1, wherein the library comprises at least 100 different surface coatings.

10. The method according to claim 1, wherein the library comprises at least 1,000 different surface coatings.

11. The method according to claim 1, wherein the library comprises at least 10,000 different surface coatings.

12. The method according to claim 1, wherein the active constituent A of compound B is a polymerized residue of a compound selected from the group consisting of:

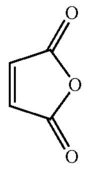

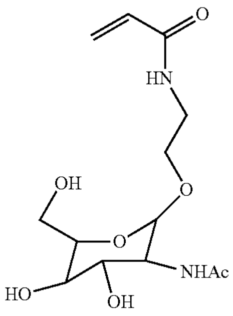

-continued
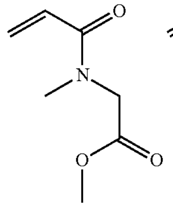
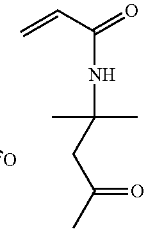
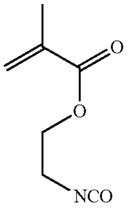
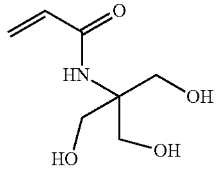
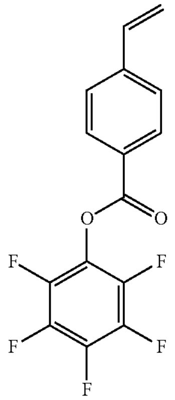
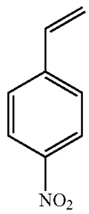
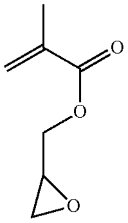
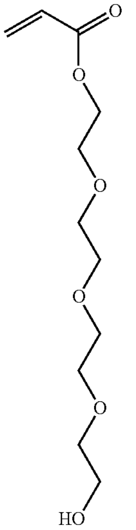
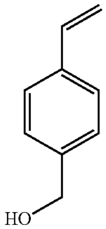
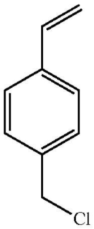
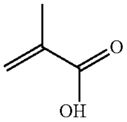
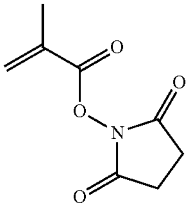
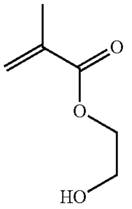
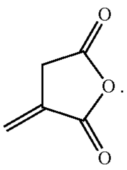
13. The method according to claim 12, wherein the active constituent A of compound B is a polymerized residue of maleic anhydride.
14. The method according to claim 1, wherein the passive constituent P of compound B is a polymerized residue of a compound selected from the group consisting of:
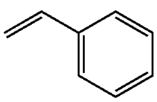
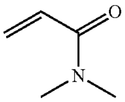
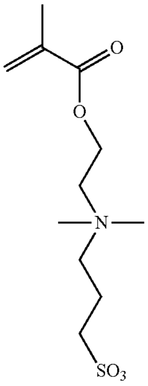
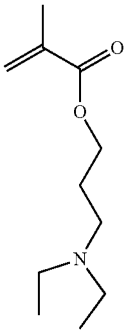
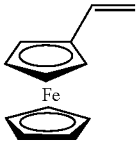
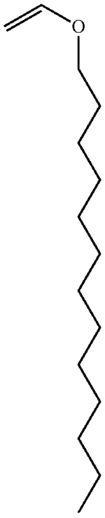
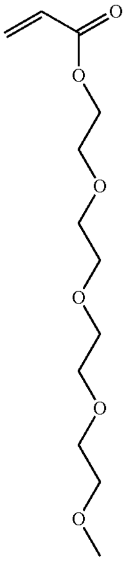
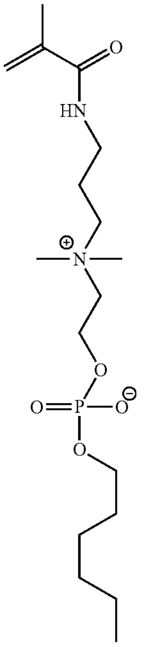
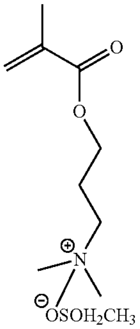

-continued

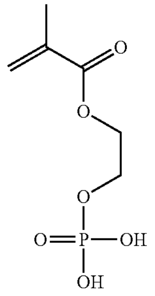

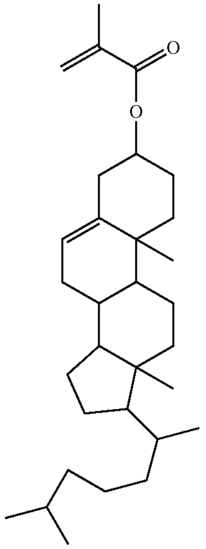

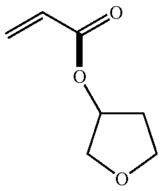

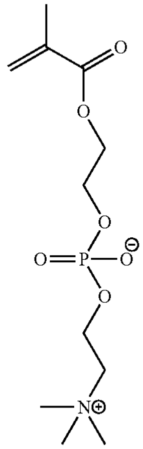

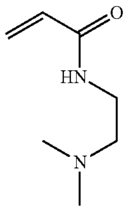

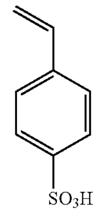

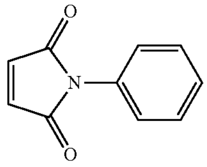

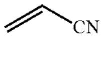

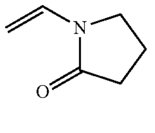

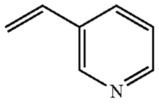

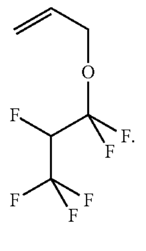

15. The method according to claim 14, wherein the passive constituent P of compound B is a polymerized residue of styrene.

16. The method according to claim 1, wherein compound B is an alternating copolymer.

17. The method according to claim 1, wherein compound B is a block copolymer of the active constituent A and the passive constituent P.

18. The method according to claim 1, wherein compound B is a copolymer of maleic anhydride and styrene.

19. The method according to claim 1, wherein compound B further comprises a control agent C.

20. The method according to claim 19, wherein the control agent is selected from a RAFT control agent, an ARTP control agent and a nitroxide control agent.

21. The method according to claim 1, wherein compound S has the structure:

X-Q-Y wherein X is the residue of an amino, hydroxyl, thiol, carboxylic acid, anhydride, isocyanate, sulfonyl chloride, sulfonic anhydride, chloroformate, ketone or aldehyde moiety; Y is the same as defined for X; and Q is a divalent organic group, and wherein X and Y are not reactive with each other or Q.

22. The method according to claim 21, wherein Q is selected from optionally substituted $C_1$ to $C_{20}$ alkylene, optionally substituted $C_2$ to $C_{20}$ alkenylene, optionally substituted $C_2$ to $C_{20}$ alkynylene and optionally substituted $C_6$ to $C_{20}$ arylene, wherein one or more carbon atoms may be substituted with a heteroatom selected from O, S or N.

23. The method according to claim 21, wherein compound S is a residue of a diamine.

24. The method according to claim 23, wherein compound S is a residue of an alkyl diamine.

25. The method according to claim 24, wherein compound S is a residue of 1,5-diaminopentane or N-(3-aminopropyl)-1,3-propanediamine.

26. The method according to claim 1, wherein compound F is a group capable of binding or chemically reacting with a biological molecule or component.

27. The method according to claim 26, wherein compound F comprises a primary or secondary amine group.

28. The method according to claim 1, wherein compound B is applied onto the substrate by the method of coating selected from the group consisting of grafting, dip coating, plasma polymerization, vapor deposition, stamp printing, gamma irradiation, electron beam exposure, and thermal and photochemical radiation.

29. The method according to claim 1, wherein compounds S and F are attached by:

1) attaching compound S to compound B and then attaching compound F to the attached compound S; or
2) attaching compound S to compound B, wherein compound S already has compound F attached to it.

30. The method according to claim 1, wherein compound B is applied onto localized regions of the substrate.

31. The method according to claim 30, wherein compound B is applied to a plurality of beads.

32. The method according to claim 1, wherein compound B is applied to the surface of the substrate, and compounds S and F are attached to compound B in localized regions.

33. The method according to claim 1, wherein the surface coatings according to the synthon which are generated on localized regions of the substrate are spatially resolved.

* * * * *